United States Patent
Moroney et al.

(10) Patent No.: US 11,725,203 B2
(45) Date of Patent: Aug. 15, 2023

(54) SMALL-MOLECULE MEDIATED SIZE SELECTION OF NUCLEIC ACIDS

(71) Applicant: QIAGEN Sciences, LLC, Germantown, MD (US)

(72) Inventors: Vince Moroney, Rancho Santa Fe, CA (US); Eddie Adams, San Diego, CA (US); Mark Brolaski, Encinitas, CA (US); Ingemar Pedron, San Diego, CA (US)

(73) Assignee: QIAGEN Sciences, LLC, Germantown, MD (US)

( * ) Notice: Subject to any disclaimer, the term of this patent is extended or adjusted under 35 U.S.C. 154(b) by 0 days.

(21) Appl. No.: 16/953,857

(22) Filed: Nov. 20, 2020

(65) Prior Publication Data

US 2021/0317434 A1 Oct. 14, 2021

Related U.S. Application Data

(62) Division of application No. 15/757,323, filed as application No. PCT/US2016/050229 on Sep. 2, 2016, now Pat. No. 10,883,099.

(60) Provisional application No. 62/214,862, filed on Sep. 4, 2015.

(51) Int. Cl.
*C12N 15/10* (2006.01)

(52) U.S. Cl.
CPC ....... *C12N 15/101* (2013.01); *C12N 15/1003* (2013.01); *C12N 15/1006* (2013.01); *C12N 15/1013* (2013.01); *C12N 15/1017* (2013.01)

(58) Field of Classification Search
CPC ............ C12N 15/1003; C12N 15/1006; C12N 15/1017
See application file for complete search history.

(56) References Cited

U.S. PATENT DOCUMENTS

| | | | |
|---|---|---|---|
| 5,705,628 A | 1/1998 | Hawkins | |
| 5,898,071 A | 4/1999 | Hawkins | |
| 6,534,262 B1 | 3/2003 | McKernan et al. | |
| 8,679,741 B2 * | 3/2014 | Hoyal-Wrightson | ........................ C12N 15/1003 435/6.1 |
| 2007/0190535 A1 | 8/2007 | Hall, Jr. et al. | |
| 2007/0202511 A1 | 8/2007 | Chen et al. | |
| 2014/0051844 A1 | 2/2014 | Forman et al. | |

FOREIGN PATENT DOCUMENTS

| | | |
|---|---|---|
| EP | 2 345 719 A1 | 7/2011 |
| WO | 2007/140417 A2 | 12/2007 |
| WO | 2014/122288 A1 | 8/2014 |
| WO | 2015/003060 A1 | 1/2015 |

* cited by examiner

*Primary Examiner* — Pancham Bakshi
(74) *Attorney, Agent, or Firm* — Seed IP Law Group LLP

(57) ABSTRACT

Provided are methods and compositions for negatively and positively selecting for different size nucleic acid (e.g., DNA or RNA) fragments on borosilicate glass fiber membranes, silica and metal oxide surfaces such that only those fragments falling within a desired size range are obtained.

28 Claims, 26 Drawing Sheets

L: Ladder, no size selection
A: Eluent of single bind only
B: Eluent of bind + secondary bind (same amount 4(Me)N acetate)
C: Flowthrough of single bind only
D: Flowthrough of bind + secondary bind (same amount 4(Me)N acetate)

FIG. 24A  FIG. 24B
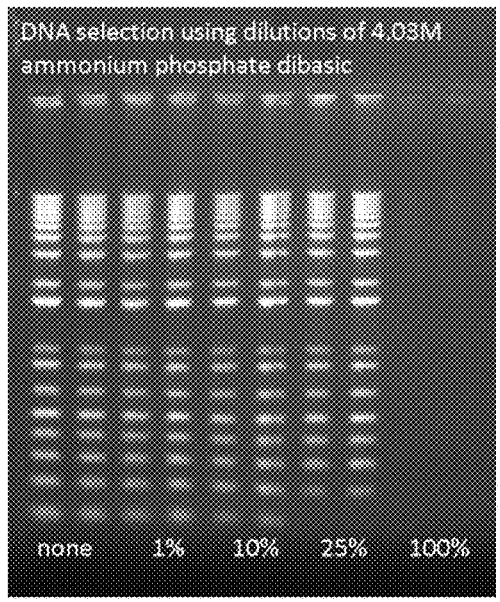
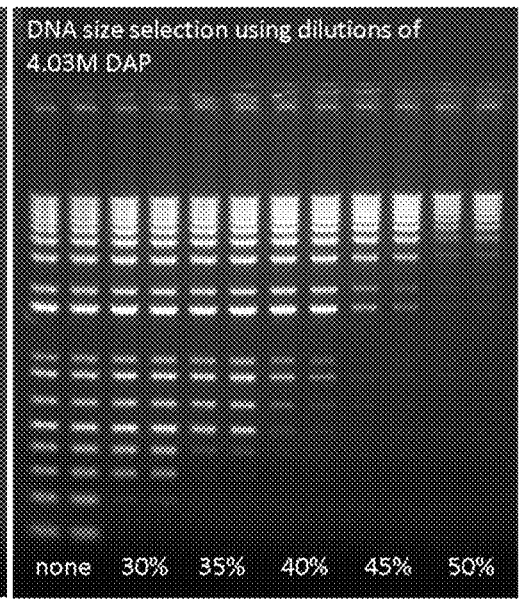
FIG. 24C
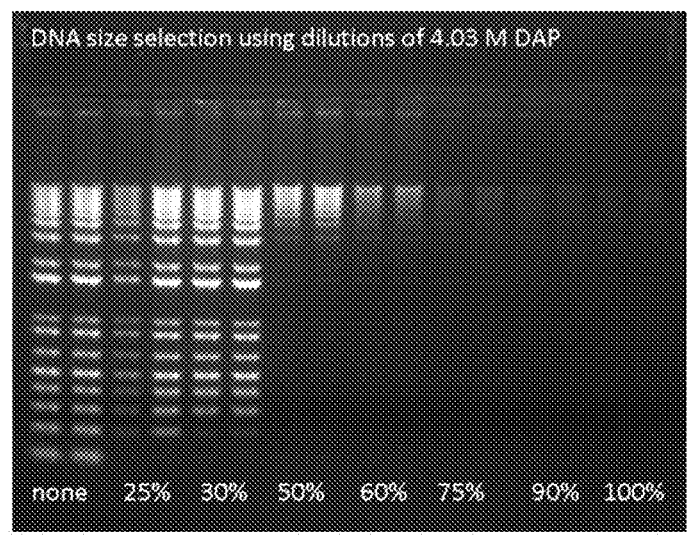

SMALL-MOLECULE MEDIATED SIZE SELECTION OF NUCLEIC ACIDS

CROSS-REFERENCE TO RELATED APPLICATIONS

The present application is a divisional of U.S. application Ser. No. 15/757,323, filed Mar. 2, 2018, which is a U.S. national phase application of PCT/US2016/050229, filed Sep. 2, 2016, which claims the benefit under 35 U.S.C. § 119(e) to U.S. Provisional Application No. 62/214,862, filed Sep. 4, 2015. U.S. application Ser. No. 15/757,323 and U.S. Provisional Application No. 62/214,862 are hereby incorporated by reference in their entirety.

FIELD

In some aspects, provided herein are methods and compositions (e.g., kits) for the size-selective isolation of nucleic acids (e.g., DNA or RNA) from a nucleic acid-containing sample. In particular embodiments, disclosed herein are methods and compositions for small-molecule mediated size selection of nucleic acids on a borosilicate glass, silica, or metal oxide surfaces.

BACKGROUND

The selective fractionation of nucleic acids (e.g., DNA or RNA) by size is an important tool in molecular biology. There is an increasing interest and need for fast, simple and reliable methods for removing undesired nucleic acid fragments from samples in the preparation of nucleic acid sequencing libraries, such as for next generation sequencing (NGS). The difference in size of nucleic acids is an important criterion in distinguishing nucleic acids of interest from nucleic acid byproducts that should be excluded.

Nucleic acids of a specific minimum and/or maximum size are used in nucleic acid library construction methods, such as for next generation sequencing applications. To ensure high quality sequencing data, efficient library preparation methods are required to reduce the background in the sequencing reads. Therefore, it is important to remove nucleic acid contaminants that might be present in the sample as a result of the library preparation. For example, small nucleic acid molecules such as adapter monomers and adapter-adapter ligation products that are often present in the sequencing library after adapter ligation must be removed prior to sequencing to reduce background in the sequencing data.

Existing methods of size-selective nucleic acid isolation are cumbersome and time-consuming. Standard methods for isolating nucleic acid molecules of a specific target size involve separation of the nucleic acid using gel electrophoresis, cutting out the gel band with the desired nucleic acid fragment size, and then extracting the nucleic acid molecules of the specific target size from the gel fragment.

Polyethylene glycol (PEG)-based buffers are also widely used in the size-selective isolation of nucleic acid fragments. However, PEG-based isolation methods are disadvantageous because of the highly viscous polyethylene glycol, which hinders the efficiency of washing the nucleic acids. Size selection of DNA fragments on carboxylic acid-coated magnetic beads driven by PEG/NaCl solutions is a well-known technique (U.S. Pat. Nos. 5,705,628, 5,898,071, and 6,534,262). However, there is a risk of bead carry-over, which may have a disadvantageous impact on downstream reactions such as subsequent enzymatic reactions. Accordingly, there is a need for additional methods for selective fractionation of nucleic acids by size.

SUMMARY

In one aspect, provided is a method of selectively isolating target nucleic acid molecules from a nucleic acid-containing sample, wherein the target nucleic acid molecules are within a particular molecular size range and non-target nucleic acid molecules are outside the molecular size range. In some embodiments, the method includes contacting a sample comprising nucleic acid molecules with a matrix in the presence of a carboxylate compound. In some embodiments, the carboxylate compound is present in sufficient concentration that the target nucleic acid molecules selectively bind to the matrix and non-target nucleic acid molecules do not bind to the matrix.

In some embodiments, greater than about 95% wt. % of the nucleic acid molecules bound to the matrix are the target nucleic acid molecules. In some embodiments, greater than about 90% wt. % of the nucleic acid molecules bound to the matrix are the target nucleic acid molecules. In other embodiments, greater than about 70% wt. % of the nucleic acid molecules bound to the matrix are the target nucleic acid molecules.

In some embodiments, the method further includes a step wherein the matrix is washed to remove the unbound nucleic acid. In some embodiments, the method further includes a step wherein the bound nucleic acid molecules are eluted from the matrix.

In some embodiments, the matrix contains silica. In some embodiments, the matrix contains borosilicate glass. In some embodiments, the matrix contains silicon dioxide. In some embodiments, the matrix contains silicon dioxide-coated magnetic beads. In other embodiments, the matrix contains a metal oxide.

In some embodiments, the carboxylate compound is of formula (I)

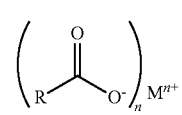

$$\left( R \underset{O^-}{\overset{O}{\bigwedge}} \right)_n M^{n+} \quad (I)$$

wherein
R is selected from the group consisting of H, substituted or unsubstituted $C_1$-$C_8$ alkyl, substituted or unsubstituted $C_1$-$C_8$ alkenyl, and substituted or unsubstituted $C_1$-$C_8$ alkynyl;
M is a metal or $N(R^a)_4$;
each $R^a$ is independently H or alkyl; and
n is 1, 2, or 3;
or a hydrate thereof.

In some embodiments, $M^{n+}$ is $Na^+$, $Li^+$, $K^+$, $Ca^{2+}$, $Mg^{2+}$, $Al^{3+}$, or $NH_4^+$. In some embodiments, R is substituted or unsubstituted $C_1$-$C_8$ alkyl. In some embodiments, R is $CH_3$. In some embodiments, R is $C_1$-$C_8$ alkyl substituted with one or more halogen.

In some embodiments, the carboxylate compound contains acetate. In some embodiments, the carboxylate compound is ammonium acetate or sodium acetate.

In some embodiments, the carboxylate compound is in a solution. In some embodiments, the solution further contains guanidine hydrochloride, Tris HCl, and isopropanol.

In some embodiments, the nucleic acid contains DNA. In other embodiments, the nucleic acid contains RNA.

In another aspect, provided is a method of selectively isolating target nucleic acid molecules from a nucleic acid-containing sample, wherein the target nucleic acid molecules are within a particular molecular size range and non-target nucleic acid molecules are outside the molecular size range, the method including:

a) contacting a sample containing nucleic acid molecules with a first matrix in the presence of a first carboxylate compound, wherein the first carboxylate compound is present in sufficient concentration that nucleic acid molecules of molecular size above the upper limit of the target molecular size range selectively bind to the matrix and nucleic acid molecules of molecular size below the upper limit of the target molecular size range do not bind to the matrix;

b) collecting all or a portion of the sample that is not bound to the first matrix;

c) contacting all or the portion of the sample that is not bound to the first matrix with a second matrix in the presence of a second carboxylate compound, wherein the second carboxylate compound is present in a sufficient concentration that nucleic acid molecules of the target molecular size range selectively bind to the second matrix and nucleic acid molecules of molecular size below the lower limit of the target molecular size range do not bind to the matrix.

In some embodiments, the concentration of the first carboxylate compound is greater than the concentration of the second carboxylate compound. In some embodiments, the nucleic acid molecules of molecular size above the upper limit of the target molecular size range are removed from the first matrix by washing or elution to produce the second matrix.

In another aspect, provided is a kit containing a carboxylate compound, a matrix, and instructions for use according to any of the methods described herein.

In another aspect, provided is a kit containing ammonium acetate, guanidine hydrochloride, and Tris HCl. In some embodiments, the ammonium acetate, guanidine hydrochloride, and Tris HCl are present in a solution. In some embodiments, the kit contains about 7.5 M ammonium acetate, about 5.2 M guanidine hydrochloride, and about 30 mM Tris HCl. In some embodiments, the kit includes a matrix. In some embodiments, the kit includes isopropanol. In some embodiments, the kit includes instructions for use according to any of the methods described herein.

In another aspect, provided is a method of selectively isolating target nucleic acid molecules from a nucleic acid-containing sample, wherein the target nucleic acid molecules are within a particular molecular size range and non-target nucleic acid molecules are outside the molecular size range, wherein the method includes contacting a sample comprising nucleic acid molecules with a matrix in the presence of a small-molecule modulator, wherein the small-molecule modulator is present in sufficient concentration that the target nucleic acid molecules selectively bind to the matrix and non-target nucleic acid molecules do not bind to the matrix.

In some embodiments, greater than about 95% wt. % of the nucleic acid molecules bound to the matrix are the target nucleic acid molecules. In some embodiments, greater than about 90% wt. % of the nucleic acid molecules bound to the matrix are the target nucleic acid molecules. In some embodiments, greater than about 70% wt. % of the nucleic acid molecules bound to the matrix are the target nucleic acid molecules.

In some embodiments, the method further includes a step wherein the matrix is washed to remove the unbound nucleic acid. In some embodiments, the method further includes a step wherein the bound nucleic acid molecules are eluted from the matrix. In some embodiments, the matrix contains silica. In some embodiments, the matrix contains borosilicate glass. In some embodiments, the matrix contains silicon dioxide. In some embodiments, the matrix contains silicon dioxide-coated magnetic beads. In some embodiments, the matrix contains a metal oxide.

In some embodiments, the small-molecule modulator contains a carboxylate moiety. In some embodiments, the small-molecule modulator contains a phosphate, phosphonate, or borate moiety. In some embodiments, the small-molecule modulator contains an ammonium or substituted ammonium moiety. In some embodiments, the small-molecule modulator is of formula (Ia)

(Ia)

wherein $R^1$ is a structural moiety that satisfies the following two conditions: 1) $R^1$ does not render the carboxylate insoluble in water at high concentration (preferably 1-8 M); and 2) $R^1$ cannot be ionized to a negative species within the range of pH 4-9; M is a metal or $N(R^a)_4$; each $R^a$ is independently H or alkyl; and n is 1, 2, or 3; or a hydrate thereof.

In some embodiments, the small-molecule modulator is of formula (Ib)

wherein $R^2$ is a phosphonate or a phosphonic acid (e.g., phosphonoacetic acid); M is a metal or $N(R^a)_4$; each $R^a$ is independently H or alkyl; and n is 1, 2, or 3; or a hydrate thereof.

In some embodiments, the small-molecule modulator is a carboxylate compound of formula (I)

(I)

wherein R is selected from the group consisting of H, substituted or unsubstituted $C_1$-$C_8$ alkyl, substituted or unsubstituted $C_1$-$C_8$ alkenyl, and substituted or unsubstituted $C_1$-$C_8$ alkynyl; M is a metal or $N(R^a)_4$; each $R^a$ is independently H or alkyl; and n is 1, 2, or 3; or a hydrate thereof. In some embodiments, R is substituted or unsubstituted $C_1$-$C_8$ alkyl. In some embodiments, R is $CH_3$. In some embodiments, R is $C_1$-$C_8$ alkyl substituted with one or more halogen.

In some embodiments, $M^{n+}$ is $Na^+$, $Li^+$, $K^+$, $Ca^{2+}$, $Al^{3+}$, or $NH_4^+$. In some embodiments, the small-molecule modulator comprises acetate. In some embodiments, the small-molecule modulator is ammonium acetate or sodium acetate. In some embodiments, the small-molecule modulator is in a solution. In some embodiments, the solution further comprises guanidine hydrochloride, Tris-HCl, and isopropanol.

In some embodiments, the nucleic acid comprises DNA. In some embodiments, the nucleic acid comprises RNA.

In another aspect, provided is a method of selectively isolating target nucleic acid molecules from a nucleic acid-containing sample, wherein the target nucleic acid molecules are within a particular molecular size range and non-target nucleic acid molecules are outside the molecular size range, the method including a) contacting a sample comprising nucleic acid molecules with a first matrix in the presence of a first small-molecule modulator, wherein the first small-molecule modulator is present in sufficient concentration that nucleic acid molecules of molecular size above the upper limit of the target molecular size range selectively bind to the first matrix and nucleic acid molecules of molecular size below the upper limit of the target molecular size range do not bind to the first matrix; b) collecting all or a portion of the sample that is not bound to the first matrix; c) contacting all or the portion of the sample that is not bound to the first matrix with a second matrix in the presence of a second small-molecule modulator, wherein the second small-molecule modulator is present in a sufficient concentration that nucleic acid molecules of the target molecular size range selectively bind to the second matrix and nucleic acid molecules of molecular size below the lower limit of the target molecular size range do not bind to the second matrix.

In some embodiments, the first small-molecule modulator is a carboxylate compound. In some embodiments, the second small-molecule modulator is a carboxylate compound. In some embodiments, the concentration of the first small-molecule modulator is greater than the concentration of the second small-molecule modulator. In some embodiments, the nucleic acid molecules of molecular size above the upper limit of the target molecular size range are removed from the first matrix by washing or elution to produce the second matrix.

In another aspect, provided is a method of selectively isolating target nucleic acid molecules from a nucleic acid-containing sample, wherein the target nucleic acid molecules are within a particular molecular size range and non-target nucleic acid molecules are outside the molecular size range, the method including: a) contacting a sample containing nucleic acid molecules with a first matrix in the absence of a small-molecule modulator such that both target and non-target nucleic acid molecules bind to the matrix; b) washing the matrix in the presence of a first small-molecule modulator, wherein the first small-molecule modulator is present in sufficient concentration that nucleic acid molecules of molecular size above the upper limit of the target molecular size range are selectively retained on the first matrix and nucleic acid molecules of molecular size below the upper limit of the target molecular size range are released from the first matrix; c) collecting all or a portion of the sample that is released from the first matrix; d) contacting all or the portion of the sample that is released from the first matrix with a second matrix in the presence of a second small-molecule modulator, wherein the second small-molecule modulator is present in a sufficient concentration that nucleic acid molecules of the target molecular size range selectively bind to the second matrix and nucleic acid molecules of molecular size below the lower limit of the target molecular size range do not bind to the second matrix.

In some embodiments, the first small-molecule modulator is a carboxylate compound. In some embodiments, the second small-molecule modulator is a carboxylate compound. In some embodiments, the concentration of the first small-molecule modulator is greater than the concentration of the second small-molecule modulator.

In another aspect, provided is a kit containing a small-molecule modulator, a matrix, and instructions for use according to any of the methods provided herein. In some embodiments, the small-molecule modulator is a carboxylate compound.

In another aspect, provided is a kit containing ammonium acetate, guanidine hydrochloride, and Tris HCl. In some embodiments, the ammonium acetate, guanidine hydrochloride, and Tris HCl are present in a solution. In some embodiments, the kit contains about 7.5 M ammonium acetate, about 5.2 M guanidine hydrochloride, about 30 mM Tris HCl. In some embodiments, the kit further contains a matrix. In some embodiments, the kit further contains isopropanol. In some embodiments, the kit further contains instructions for use according to any of the methods provided herein.

M, and 1.5 M guanidine HCl were used. In this gel, the different nucleic acid binding solutions was held constant at 170 μL and DNA sample was held constant at 50 μL.

Figure 22A:
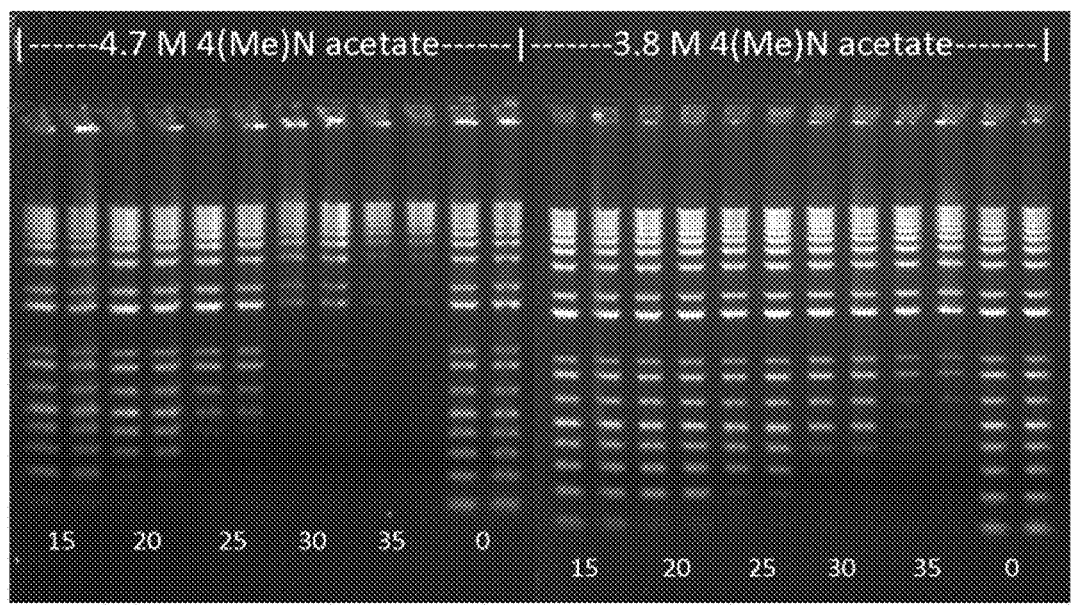

FIG. 22A compares the electrophoretic separation of 1 kb DNA molecular weight ladder samples subjected to different concentrations of DNA bind modifier during the binding reaction using borosilicate glass spin filters. Increasing amounts of 4.7 M and 3.8 M tetramethyl ammonium acetate were used as DNA bind modifiers. In this gel, the nucleic acid binding solution was held constant at 170 μL while DNA bind modifier volumes were varied from 0 to 35 μL.

Figure 22B:
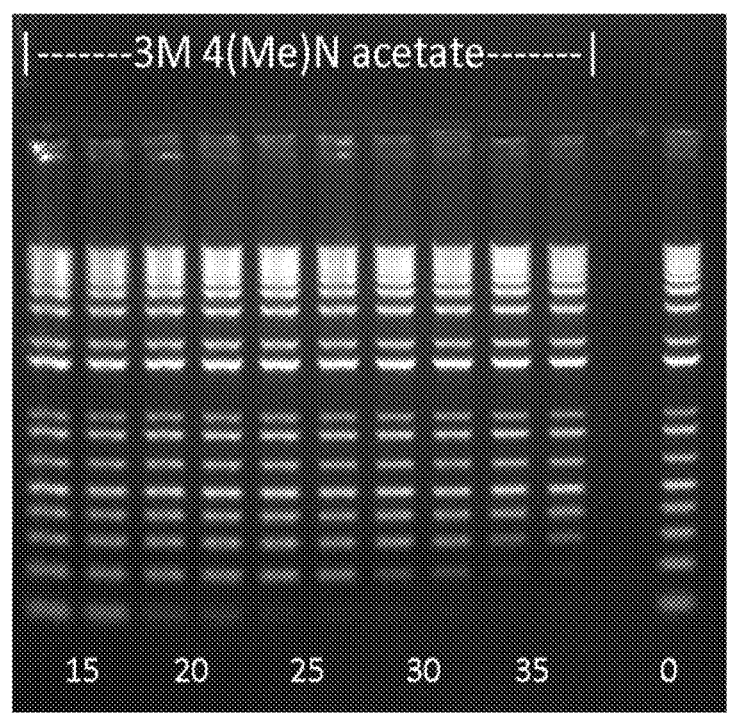

FIG. 22B compares the electrophoretic separation of 1 kb DNA molecular weight ladder samples subjected to increasing amounts of DNA bind modifier during the binding reaction using borosilicate glass spin filters. 3 M tetramethyl ammonium acetate was used as DNA bind modifier. In this gel, the nucleic acid binding solution was held constant at 170 while DNA bind modifier volumes were varied from 0 to 35 μL.

Figure 23:
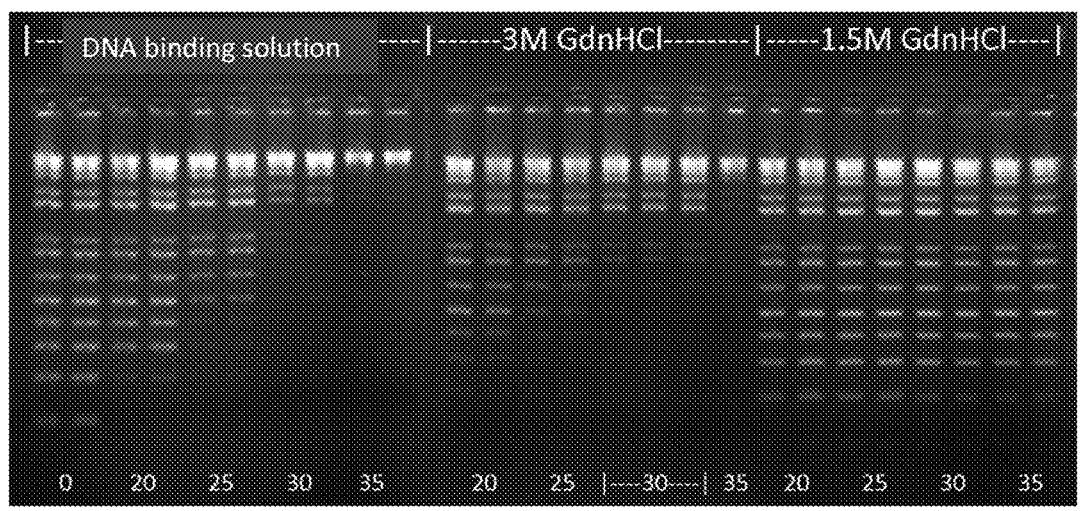

FIG. 23 compares the electrophoretic separation of 1 kb DNA molecular weight ladder samples subjected to DNA binding solutions with different guanidine HCl concentrations in the presence or absence of increasing amounts of DNA bind modifier (4.67 M tetramethyl ammonium acetate) during the binding reaction using borosilicate glass spin filters. DNA binding solutions with 1.5 M and 3 M guanidine HCl were used. In this gel, the different DNA binding solutions was held constant at 170 μL and DNA sample was held constant at 50 μL.

FIG. 24A compares the electrophoretic separation of 1 kb DNA molecular weight ladder samples in the absence or presence of increasing amounts of diammonium phosphate (DAP) during the binding reaction using borosilicate glass spin filters. Different dilutions of 4.03 M DAP were used as DNA bind modifier. 50 μL of DNA ladder was combined with 170 of DNA binding solution and DAP amount was kept constant at 35 μL (DAP dilutions were varied from 1 to 100%).

FIG. 24B compares the electrophoretic separation of 1 kb DNA molecular weight ladder samples in the absence or presence of increasing amounts of diammonium phosphate (DAP) during the binding reaction using borosilicate glass spin filters. Different dilutions of 4.03 M DAP were used as DNA bind modifier. 50 μL of DNA ladder was combined with 170 of nucleic acid binding solution and DAP amount was kept constant at 35 μL (DAP dilutions were varied from 30 to 50%).

FIG. 24C compares the electrophoretic separation of 1 kb DNA molecular weight ladder samples in the absence or presence of increasing amounts of diammonium phosphate (DAP) during the binding reaction using borosilicate glass spin filters. Different dilutions of 4.03 M DAP were used as DNA bind modifier. 50 μL of DNA ladder was combined with 170 of DNA binding solution and DAP amount was kept constant at 35 μL (DAP dilutions were varied from 25 to 100%).

Figure 25:
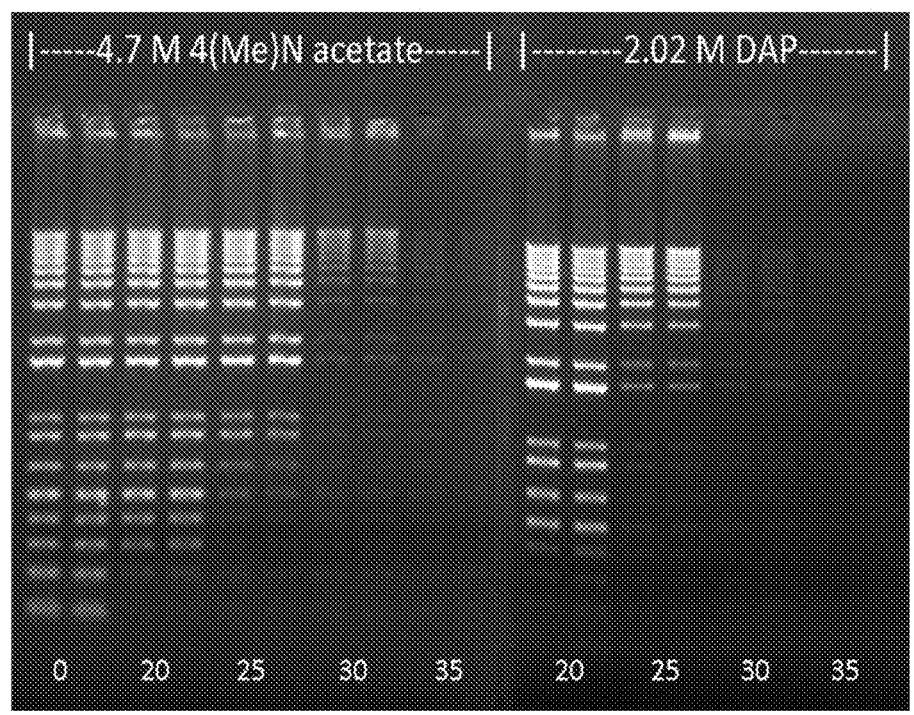

FIG. 25 compares electrophoretic separation of 1 kb DNA molecular weight ladder samples contacted with silica-coated magnetic beads (SwiftMag® beads) in the presence or absence of DNA bind modifier. Different amounts of 4.7 M tetramethyl ammonium acetate and 2.02 M diammonium phosphate (DAP) were used as DNA bind modifier. 50 μL of DNA ladder was combined with 170 μL DNA Binding Solution and 0-35 μL of DNA bind modifier.

Figure 26:
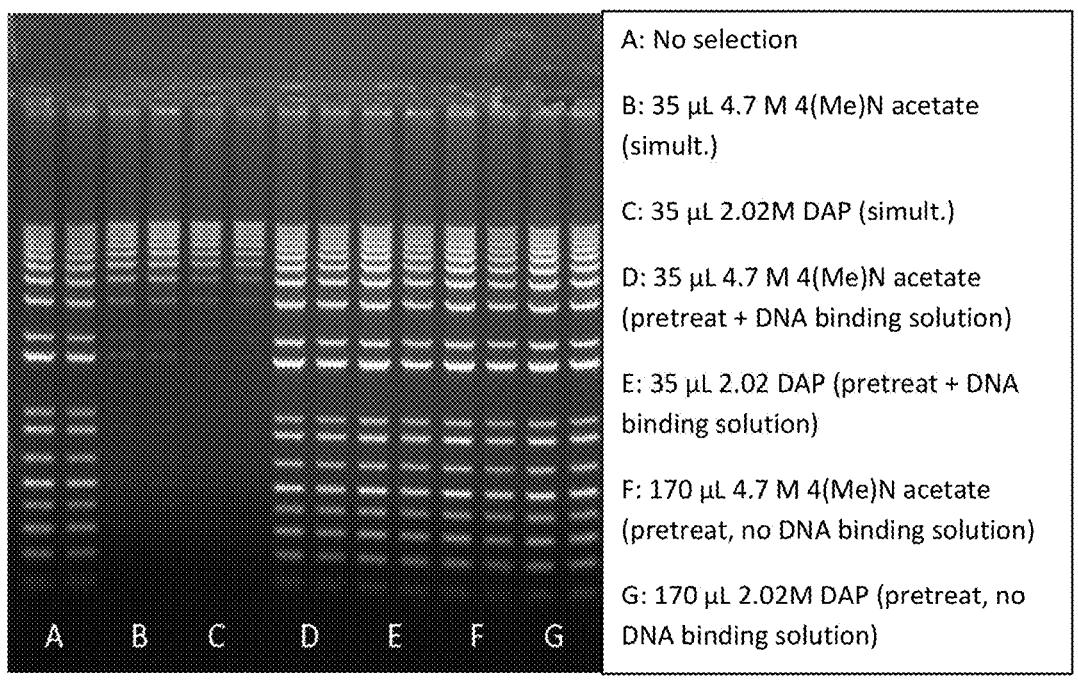

FIG. 26 compares the electrophoretic separation of 1 kb DNA molecular weight ladder samples in the presence or absence of DNA bind modifier during the binding reaction using borosilicate glass spin filters with or without pretreatment with the DNA bind modifier. 4.7 M tetramethyl ammonium acetate and 2.02 M diammonium phosphate (DAP) were used as DNA bind modifiers. Sample A was a control sample that did not contain DNA bind modifier. 50 μL of DNA ladder was combined with 170 μL of DNA binding solution and 35 μL of DNA bind modifier in Samples B and C. In Samples D and E, a mixture of 50 μL of DNA ladder, 170 of DNA binding solution, and 35 μL of the indicated DNA bind modifier was subjected to a spin filter pretreated with 35 μL of the same DNA bind modifier and 170 μL DNA binding solution. In Samples F and G, a mixture of 50 μL of DNA ladder, 170 μL of DNA binding solution, and 35 μL of the indicated DNA bind modifier was subjected to a spin filter pretreated with 170 of the same DNA bind modifier.

DETAILED DESCRIPTION

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y., all of which are herein incorporated in their entireties by reference for all purposes.

In one aspect, provided herein are methods and compositions for the size-selective isolation of nucleic acid molecules (e.g., DNA or RNA) from a nucleic acid-containing sample (e.g., a biological sample). In another aspect, provided herein are methods and compositions for isolating nucleic acid molecules of a target size range from a nucleic acid-containing sample. This technique is useful, for example, in the preparation of next generation sequencing libraries as it allows very large barcoded and/or ligated PCR primers and any unintended PCR side products to be removed from the reaction mix prior to the sequencing reactions.

The methods and compositions provided herein can be used for negatively and/or positively selecting for nucleic acid molecules in a particular size range. In some embodiments, the target nucleic acid molecules have a size range with a lower size limit. For example, the target nucleic acid molecules are more than about 1 kb in length (i.e., 1000 base pair). In some embodiments, the target nucleic acid molecules have a size range with an upper size limit. For example, the target nucleic acid molecules are less than about 5 kb in length. In some embodiments, the target nucleic acid molecules have a size range with both a lower size limit and an upper size limit. For example, the target nucleic acid molecules are between about 1 kb and about 5 kb in length.

In some aspects, provided herein are methods and compositions for size selection via small-molecule modulation of nucleic acid binding to a borosilicate or a silica surface. In one aspect, in the absence of the small-molecule modulator, all nucleic acid sizes bind. When the small-molecule modulator is introduced, nucleic acid binding is reduced in a size-dependent fashion, giving this process a great deal of synthetic control. In some aspects, the small-molecule modulator is a carboxylate molecule, for example, a carboxylate anion. In one aspect, in the absence of the exogenous carboxylate anion, all nucleic acid sizes bind. When carboxylate anion is introduced, nucleic acid binding is reduced in a size-dependent fashion, giving this process a great deal of synthetic control.

In some aspects, the small-molecule modulator is a cation. For instance, a small-molecule modulator may contain a positively charged functional group that can participate in electrostatic interactions with the phosphodiester backbone of DNA and/or RNA. Cations include, without limitation, ammonium and substituted ammonium cations, such as ammonium, tetramethylammonium, choline (N,N,N-tetramethylethanolammonium), and tris(2-hydroxyethyl)methylammonium. Cations provided herein may further contain or be associated with any appropriate anion, including, without limitation, acetate, phosphate, chloride, sulfate, methylsulfate, or silicate. Particular small-molecule modulators include ammonium acetate, ammonium chloride, tetramethylammonium acetate, tetramethylammonium acetate tetrahydrate, ammonium phosphate dibasic, choline chloride, tris(2-hydroxyethyl)methylammonium methylsulfate (TMAMS), tetramethylammonium silicate, and ammonium sulfate.

In another aspect, the small-molecule modulator is an oxyanion. For instance, the oxyanion may be able to directly compete with nucleic acid phosphates for binding sites on the silica resin. Oxyanions include phosphates, phosphonates, and borates. Oxyanions may have one or more sites of deprotonation, such as one, two, or three sites of deprotonation. Oxyanions provided herein may further contain or be associated with any appropriate cation. Particular small-molecule modulators include monopotassium phosphate, dipotassium phosphate, tripotassium phosphate, monosodium phosphate, disodium phosphate, trisodium phosphate, 3-aminopropylphosphonic acid, and (aminomethyl)phosphonic acid.

In another aspect, the small-molecule modulator is a compound containing both a cation and an oxyanion covalently attached to one another. The compound may contain any cation provided herein and any oxyanion provided herein, which are covalently attached to one another. Particular small-molecule modulators are compounds that contain both a carboxylate, phosphate, phosphonate, or borate moiety covalently attached to an ammonium or substituted ammonium moiety.

Provided in some embodiments is a method of isolating nucleic acid molecules from a sample according to molecular weight. In some embodiments, the nucleic acid molecules originate from a biological sample. In some embodiments, the nucleic acids have been processed, for example, the nucleic acids have been amplified using a method such as PCR. Nucleic acids isolated using the methods and kits provided herein may be used in the areas of molecular biological application, including, for example, analytical, cloning, diagnostic, and detection. In some embodiments, the isolated nucleic acids are used as part of a sequencing library for next generation sequencing.

In some embodiments, the nucleic acid sample to be isolated comprises DNA. In some embodiments, the nucleic acid sample comprises RNA. In some embodiments, the nucleic acid sample to be isolated comprises DNA and RNA. In some embodiments, the nucleic acid (e.g., DNA or RNA) is in any naturally occurring modification thereof, or combinations thereof. In some aspects, the nucleic acid is genomic DNA and may be in a single or double stranded or in any other form.

Provided in some embodiments is a method of selectively isolating target nucleic acid molecules from a nucleic acid-containing sample. In some embodiments, the target nucleic acid molecules are within a particular molecular size range and non-target nucleic acid molecules are outside the molecular size range. In some embodiments, the sample comprising nucleic acid molecules are placed in contact with a matrix in the presence of a carboxylate compound. In some embodiments, the target nucleic acid molecules selectively bind to the matrix and the non-target nucleic acid molecules do not bind to the matrix. In some embodiments, the method further comprises a step wherein the matrix is washed to remove the unbound nucleic acid. In some embodiments, the method further comprises a step wherein the bound target nucleic acid molecules can be collected by eluting the bound nucleic acid molecules from the matrix.

In some embodiments, the target nucleic acid molecules are of a particular molecular size range. In some embodiments, the target nucleic acid molecules are greater than a particular size cut-off. In some embodiments, the target nucleic acid molecules are greater than about 100-5000 bp, such as greater than about 5000 bp, greater than about 4000 bp, greater than about 3000 bp, greater than about 2000 bp, greater than about 1500 bp, greater than about 1000 bp, greater than about 600 bp, greater than about 400 bp, or greater than about 200 bp.

It is to be understood that while the terms "target nucleic acid molecules" and "non-target nucleic acid molecules" are used herein for the purpose of illustration, the non-target nucleic acid molecules isolated from the target nucleic acid molecules can nonetheless be useful for a downstream application.

In some embodiments, a sample containing the nucleic acid molecules is contacted with a matrix in the presence of a carboxylate compound. In some embodiments, the matrix comprises silica. In some embodiments, the matrix comprises borosilicate glass. In some embodiments, the matrix comprises silicon dioxide. In some embodiments, the matrix comprises silicon dioxide-coated magnetic beads. In some embodiments, the matrix comprises SwiftMag® beads. In some embodiments, the matrix comprises a metal oxide. Exemplary metal oxides are iron oxide and magnesium oxide.

In some embodiments, the carboxylate compound is in a solution. In some embodiments, the carboxylate is soluble in water at concentrations of up to 32 M. In some embodiments, the carboxylate is soluble in water at concentrations of up to 16 M. In some embodiments, the carboxylate is soluble in water at concentrations of up to 8 M (e.g., up to 6 M, up to 4 M, up to 2 M, or up to 1 M). In some embodiments, the R group of the carboxylate cannot be ionized to a negative species within the range of pH 4-9 (e.g., pH 4-6, 5-7, 6-8, or 7-9).

In some embodiments, the small-molecule modulator is attached to the matrix. In some embodiments, the carboxylate compound is attached to the matrix.

In some embodiments, the carboxylate compound is of the formula (Ia):

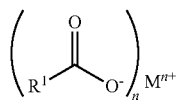

(Ia)

wherein $R^1$ is a structural moiety that satisfies the following two conditions: 1) $R^1$ does not render the carboxylate insoluble in water at high concentration (preferably 1-8 M); and 2) $R^1$ cannot be ionized to a negative species within the range of pH 4-9; M is a metal or $N(R^a)_4$; each $R^a$ is independently H or alkyl; and n is 1, 2, or 3; or a hydrate thereof.

In some embodiments, the carboxylate compound is of the formula (Ib):

$$(R^2)_n M^{n+} \quad (Ib)$$

wherein $R^2$ is a phosphonate or a phosphonic acid (e.g., phosphonoacetic acid); M is a metal or $N(R^a)_4$; each $R^a$ is independently H or alkyl; and n is 1, 2, or 3; or a hydrate thereof.

In some embodiments, the carboxylate compound is of the formula (I):

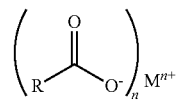

(I)

wherein
R is selected from the group consisting of H, substituted or unsubstituted $C_1$-$C_8$ alkyl, substituted or unsubstituted $C_1$-$C_8$ alkenyl, and substituted or unsubstituted $C_1$-$C_8$ alkynyl;
M is a metal or $N(R^a)_4$;
each $R^a$ is independently H or alkyl; and
n is 1, 2, or 3;
or a hydrate thereof.

In some embodiments, R is H. In some embodiments, R is unsubstituted $C_1$-$C_8$ alkyl. In some embodiments, R is $CH_3$. In some embodiments, R is a substituted $C_1$-$C_8$ alkyl. In some embodiments, R is $C_1$-$C_8$ alkyl substituted with one or more halogen. In some embodiments, R is $C_1$-$C_8$ perhaloalkyl, such as trifluoromethyl or trichloromethyl. In some embodiments, R is substituted or unsubstituted $C_1$-$C_8$ alkenyl. In some embodiments, R is substituted or unsubstituted $C_1$-$C_8$ alkynyl.

In some embodiments, the compound of any of formula (Ia), (Ib), or (I) is soluble in water at concentrations of up to 8 M (e.g., up to 6 M, up to 4 M, up to 2 M, or up to 1 M). In some embodiments, the R group of the compound of formula (I) cannot be ionized to a negative species within the range of pH 4-9 (e.g., pH 4-6, 5-7, 6-8, or 7-9).

In some embodiments of any of formulae (Ia), (Ib), and (I), M is an alkali metal such as Li, Na or K. In some embodiments, M is an alkaline earth metal such as Ca or Mg. In other embodiments, M is a metalloid such as Al. In some embodiments, M is $N(R^a)_4$. In some such embodiments, one $R^a$ group is alkyl (e.g., methyl or ethyl), and the other $R^a$ groups are H. In some such embodiments, two $R^a$ groups are independently alkyl (e.g., methyl or ethyl), and the other $R^a$ groups are H. In some such embodiments, three $R^a$ groups are independently alkyl (e.g., methyl or ethyl), and the other $R^a$ group is H. In some such embodiments, all four $R^a$ groups are independently alkyl (e.g., methyl or ethyl). In some embodiments, M is $NH_4$. In some embodiments, $M^{n+}$ is a monovalent cation, such that n=1. In other embodiments, $M^{n+}$ is a multivalent cation, such that n=2 or 3. In some embodiments, $M^{n+}$ is $Na^+$, $Li^+$, $K^+$, $Ca^{2+}$, $Mg^{2+}$, $Al^{3+}$, or $NH_4^+$.

In some embodiments, the sample comprising nucleic acid molecules is placed in contact with the small-molecule modulators prior to contact with the matrix. In some embodiments, the sample comprising nucleic acid molecules is placed in contact with the matrix prior to contact with the small-molecule modulators. In some embodiments, the small-molecule modulators are contacted with the matrix prior to contact with the sample comprising the nucleic acid molecules. In other embodiments, the sample containing the nucleic acid molecules is simultaneously contacted with the small-molecule modulators and the matrix.

In some embodiments, the concentration of the small-molecule modulator affects the binding selectivity of the target nucleic acid molecules to the matrix. In some embodiments, the small-molecule modulator is present in sufficient concentration that the target nucleic acid molecules selectively bind to the matrix. In some embodiments, the non-target nucleic acid molecules do not bind to the matrix. In some embodiments, nucleic acid molecules having a size above a certain molecular weight range bind to the matrix while nucleic acid molecules having a size below that molecular weight range do not bind to the matrix. In some embodiments, increasing the concentration of the small-molecule modulator increases the molecular weight cut-off for nucleic acid molecules that bind to the matrix.

In some embodiments, the small-molecule modulator is in a solution. In some embodiments, the small-molecule modulator can be added to a nucleic acid binding solution. In some embodiments, the nucleic acid binding solution may further comprise one or more additional components, such as a buffering agent, a chelating agent, a salt, or an additional solvent. Examples of buffering agents include, but are not limited to, Tris, PBS, MOPS, MES, and HEPES. Examples of chelating agent include, but are not limited to, EDTA, EGTA, DTPA, and BAPTA. Examples of salts include, but are not limited to guanidine hydrochloride, Tris-HCl, NaCl, $NH_4Cl$, $MgCl_2$, $KH_2PO_4$, and $K_2HPO_4$. Further examples of salts include guanidine carbonate, guanidine phosphate, guanidine sulfate, and guanidine thiocyanate. Examples of additional solvents include, but are not limited to, water-miscible protic or aprotic solvents of the appropriate dielectric constant such as ketones (e.g., acetone), alcohols (e.g., methanol, ethanol, isopropanol, and butanol) and dimethylsulfoxide. In some embodiments, the nucleic acid binding solution comprises guanidine hydrochloride, Tris-HCl, and isopropanol. In some embodiments, the small-molecule modulator is present in a sufficient concentration to promote binding of the nucleic acid molecules to the matrix. In some embodiments, the small-molecule modulator is in a concentration in the range of about 0.01 M to about 8 M, such as about 0.05 M to about 7 M, about 0.1 M to about 6 M, about 0.2 M to about 5 M, about 0.5 M to about 4 M, about 0.75 M to about 3 M, and about 1 M to about 2 M. In some embodiments the small-molecule modulator is in a concentration below about 32 M, such as below about 16 M, below about 8 M, below about 6 M, below about 4 M, below about 2 M, or below about 1 M. In some embodiments the small-molecule modulator is in a concentration above about 32 M, such as above about 16 M, above about 8 M, above about 6 M, above about 4 M, above about 2 M, above about 1 M, above about 0.5 M, or above about 0.1 M.

In some embodiments, the carboxylate compound is selected from the group consisting of ammonium acetate, sodium acetate, sodium formate, sodium propanoate, sodium trimethylacetate hydrate, sodium trichloroacetate, and sodium trifluoroacetate. In some embodiments, a combination of the various carboxylate compounds disclosed herein is used. In some embodiments, a combination of the various small-molecule modulators disclosed herein is used.

In some embodiments, the sample comprising nucleic acid molecules is placed in contact with the carboxylate compounds prior to contact with the matrix. In some embodiments, the sample comprising nucleic acid molecules is placed in contact with the matrix prior to contact with the carboxylate compounds. In some embodiments, the carboxylate compounds are contacted with the matrix prior to contact with the sample comprising the nucleic acid molecules. In other embodiments, the sample containing the nucleic acid molecules is simultaneously contacted with the carboxylate compounds and the matrix.

In some embodiments, the concentration of the carboxylate compound affects the binding selectivity of the target nucleic acid molecules to the matrix. In some embodiments, the carboxylate compound is present in sufficient concentration that the target nucleic acid molecules selectively bind to the matrix. In some embodiments, the non-target nucleic acid molecules do not bind to the matrix. In some embodiments, nucleic acid molecules having a size above a certain molecular weight range bind to the matrix while nucleic acid molecules having a size below that molecular weight range do not bind to the matrix. In some embodiments, increasing the concentration of the carboxylate compound increases the molecular weight cut-off for nucleic acid molecules that bind to the matrix.

In some embodiments, the carboxylate compound is in a solution. In some embodiments, the carboxylate compound can be added to a nucleic acid binding solution. In some embodiments, the nucleic acid binding solution may further comprise one or more additional components, such as a buffering agent, a chelating agent, a salt, or an additional solvent. Examples of buffering agents include, but are not limited to, Tris, PBS, MOPS, MES, and HEPES. Examples of chelating agent include, but are not limited to, EDTA, EGTA, DTPA, and BAPTA. Examples of salts include, but are not limited to guanidine hydrochloride, Tris-HCl, NaCl, $NH_4Cl$, $MgCl_2$, $KH_2PO_4$, and $K_2HPO_4$. Further examples of salts include guanidine carbonate, guanidine phosphate, guanidine sulfate, and guanidine thiocyanate. Examples of additional solvents include, but are not limited to, water-miscible protic or aprotic solvents of the appropriate dielectric constant such as ketones (e.g., acetone), alcohols (e.g., methanol, ethanol, isopropanol, and butanol) and dimethylsulfoxide. In some embodiments, the nucleic acid binding solution comprises guanidine hydrochloride, Tris-HCl, and isopropanol. In some embodiments, the carboxylate compound is present in a sufficient concentration to promote binding of the nucleic acid molecules to the matrix. In some embodiments, the carboxylate compound is in a concentration in the range of about 0.01 M to about 8 M, such as about 0.05 M to about 7 M, about 0.1 M to about 6 M, about 0.2 M to about 5 M, about 0.5 M to about 4 M, about 0.75 M to about 3 M, and about 1 M to about 2 M. In some embodiments the carboxylate compound is in a concentration below about 32 M, such as below about 16 M, below about 8 M, below about 6 M, below about 4 M, below about 2 M, or below about 1 M. In some embodiments the carboxylate compound is in a concentration above about 32 M, such as above about 16 M, above about 8 M, above about 6 M, above about 4 M, above about 2 M, above about 1 M, above about 0.5 M, or above about 0.1 M.

In some embodiments, the matrix is washed to remove the unbound nucleic acid molecules. In some embodiments, the matrix is washed using a wash buffer. In some embodiments, the wash buffer is an aqueous solution that may comprise one or more components, such as a buffering agent, a chelating agent, a salt, or an additional solvent. Examples of buffering agents include, but are not limited to, Tris, PBS, MOPS, IVIES, and HEPES. Examples of chelating agent include, but are not limited to, EDTA, EGTA, DTPA, and BAPTA. Examples of salts include, but are not limited to NaCl, $NH_4Cl$, $MgCl_2$, $KH_2PO_4$, and $K_2HPO_4$. Examples of additional solvents include, but are not limited, water-miscible protic or aprotic solvents of the appropriate dielectric constant such as ketones (e.g., acetone), alcohols (e.g., methanol, ethanol, isopropanol, and butanol) and dimethylsulfoxide. In some embodiments, the wash buffer comprises one or more of Tris, EDTA, NaCl, and ethanol. In some embodiments, the wash buffer has a pH of between about 7 and about 8, such as between about pH 7.4-7.9.

In some embodiments, the nucleic acid molecules bound to the matrix are eluted from the matrix using an eluent. In some embodiments, the nucleic acid molecules bound to the matrix are eluted with PCR-grade water. In some embodiments, the nucleic acid molecules bound to the matrix are eluted with a buffering agent, such as Tris, PBS, MOPS, MES, HEPES, or any combination thereof. In other embodiments, the nucleic acid molecules bound to the matrix are eluted with Tris(hydroxymethyl)aminomethane (Tris) solution. In some embodiments, the pH of the eluent is between about 7-9, such as about 8.

In some embodiments, any of the methods described herein are performed in the absence of polyethylene glycol (PEG).

In some embodiments, the method provides conditions that inhibit the binding of non-target nucleic acid molecules to the matrix, wherein the non-target nucleic acid molecules are below a certain molecular weight cut-off value. In some embodiments, nucleic acid molecules having a size above a certain cut-off value bind to the matrix while nucleic acid molecules having a size below a certain cut-off value do not bind to the matrix. In some embodiments, the cut-off value lies in the range of about 5000-12000 bp, such as about 8000-12000 bp, about 6000-9000 bp, or about 5000-7000 bp. In some embodiments, the cut-off value lies in the range of about 2000-6000 bp, such as about 4000-6000 bp, about 3000-5000 bp, or about 2000-4000 bp. In some embodiments, the cut-off value lies in the range of about 500-3000 bp, such as about 1500-3000 bp, 1000-2000 bp, or 500-1000 bp. In some embodiments, the cut-off value lies in the range of about 100-1000 bp, such as between about 700-1000 bp, between about 500-800 bp, between about 300-600 bp, or between about 100-400 bp. In some embodiments, the cut-off value is about 12,000 bp, about 10,000 bp, about 7,000 bp, about 5,000 bp, about 3,000 bp, about 2,000 bp, about 1,500 bp, about 1,000 bp, about 850 bp, about 650 bp, about 500 bp, about 400 bp, about 300 bp, about 200 bp, or about 100 bp.

In some embodiments, the target nucleic acid molecules are within a particular molecular weight range and the non-target nucleic acid molecules are outside the molecular weight range. In some embodiments, greater than about 99% wt. % of the nucleic acid molecules that bind to the matrix are the target nucleic acid molecules. In some embodiments, greater than about 95% wt. % of the nucleic acid molecules that bind to the matrix are the target nucleic acid molecules. In some embodiments, greater than about 90% wt. % of the nucleic acid molecules that bind to the matrix are the target nucleic acid molecules. In some embodiments, greater than about 80% wt. % of the nucleic acid molecules that bind to the matrix are the target nucleic acid molecules. In some embodiments, greater than about 70% wt. % of the nucleic acid molecules that bind to the matrix are the target nucleic acid molecules. In some embodiments, greater than about 60% wt. % of the nucleic acid molecules that bind to the matrix are the target nucleic acid molecules. In some embodiments, greater than about 50% wt. % of the nucleic acid molecules that bind to the matrix are the target nucleic acid molecules.

In some embodiments, greater than about 99% of the nucleic acid molecules that bind to the matrix are the target nucleic acid molecules. In some embodiments, greater than about 95% of the nucleic acid molecules that bind to the matrix are the target nucleic acid molecules. In some embodiments, greater than about 90% of the nucleic acid molecules that bind to the matrix are the target nucleic acid molecules. In some embodiments, greater than about 80% of the nucleic acid molecules that bind to the matrix are the target nucleic acid molecules. In some embodiments, greater than about 70% of the nucleic acid molecules that bind to the matrix are the target nucleic acid molecules. In some embodiments, greater than about 60% of the nucleic acid molecules that bind to the matrix are the target nucleic acid molecules. In some embodiments, greater than about 50% of the nucleic acid molecules that bind to the matrix are the target nucleic acid molecules.

In some embodiments, the nucleic acid molecules that bind to the matrix are utilized in further processes or analytical methods. In some embodiments, the nucleic acid molecules that do not bind to the matrix are utilized in further processes or analytical methods. In some embodiments, nucleic acid molecules above a certain molecular weight range can be obtained by collecting the nucleic acid molecules that are bound to the matrix. In some embodiments, nucleic acid molecules below a certain molecular weight can be obtained by collecting the nucleic acid molecules that are not bound to the matrix (i.e., that are eluted from the matrix).

In other embodiments, nucleic acid molecules within a particular molecular size range, e.g., nucleic acid molecules that have molecular weight of intermediate value, can be obtained by using a double-sided selection method. In some embodiments, the double sided selection method comprises two or more steps. In some embodiments, the double-sided selection method requires the use of two or more separate matrices. In some embodiments, the two or more matrices used in the double-sided selection method have the same composition. In some embodiments, the two or more matrices used in the double-sided selection method are different in composition. In some embodiments, the double-sided selection method comprises a first step of removing the larger nucleic acid molecules (i.e., nucleic acid molecules that are above the desired size range) by contacting the nucleic acid-containing sample with a first matrix in the presence of a first carboxylate compound in a concentration that is sufficient for selectively binding the larger nucleic acid molecules to the first matrix. In some embodiments, the doubled-sided selection method comprises washing the first matrix to collect the unbound nucleic acid molecules for further processing. In some embodiments, the first matrix with the bound nucleic acid molecules from the first step is discarded. In some embodiments, the double-sided selection method comprises a further step of removing the smaller nucleic acid molecules (i.e., nucleic acid molecules that are below the desired size range), wherein the unbound nucleic acid molecules from the first step are contacted with a second matrix in the presence of a second carboxylate compound in a concentration that is sufficient to selectively remove smaller nucleic acid molecules that are not bound to the second matrix. In some embodiments, the second matrix is washed to remove the unbound nucleic acid molecules. In some embodiments, the second matrix is eluted to obtain the nucleic acid molecules within the desired size range (e.g., that are intermediate in size).

In some embodiments, the double-sided selection method comprises a first step of removing smaller nucleic acid molecules (i.e., nucleic acid molecules that are below the desired size range) by contacting the nucleic acid-containing sample with a first matrix in the presence of a first carboxylate compound in a concentration that is sufficient for selectively binding larger nucleic acid molecules. In some embodiments, the doubled-sided selection method comprises washing the first matrix to remove the unbound smaller nucleic acid molecules from the first matrix. In some embodiments, the first matrix with the bound larger nucleic acid molecules is contacted with a second carboxylate compound of a different concentration such that nucleic acid molecules that are above the desired size range remain bound to the first matrix while nucleic acids of the desired size range are washed from the matrix. In other embodiments, the first matrix with the bound nucleic acid molecules from the first step is eluted, and the eluted nucleic acid molecules are further processed. In some embodiments, the double-sided selection method comprises a further step of removing the larger nucleic acid molecules (i.e., nucleic acid molecules that are above the desired size range), wherein the eluted nucleic acid molecules from the first step are contacted with a second matrix in the presence of a second carboxylate compound in a concentration that is sufficient to selectively bind the larger nucleic acid molecules (i.e., nucleic acid molecules that are above the desired size range) that are still present. In some embodiments, the unbound nucleic acid molecules are collected. In some embodiments, the second matrix is washed to obtain the unbound nucleic acid molecules. In some embodiments, the unbound nucleic molecules are within the desired size range (e.g., are intermediate in size).

In some embodiments, the concentration of small-molecule modulator used in the first step is greater than the concentration of small-molecule modulator used in the second step. In some embodiments, the concentration of small-molecule modulator used in the first step is less than the concentration of small-molecule modulator used in the second step. In some embodiments, the concentration of small-molecule modulator used in each step of the double-sided selection method can be adjusted to obtain nucleic acid molecules between a certain molecular range, wherein the molecular range has a lower molecular weight cut-off limit and a higher molecular weight cut-off limit.

In some embodiments, the concentration of carboxylate compound used in the first step is greater than the concentration of carboxylate compound used in the second step. In some embodiments, the concentration of carboxylate compound used in the first step is less than the concentration of carboxylate compound used in the second step. In some embodiments, the concentration of carboxylate compound used in each step of the double-sided selection method can be adjusted to obtain nucleic acid molecules between a certain molecular range, wherein the molecular range has a lower molecular weight cut-off limit and a higher molecular weight cut-off limit.

Provided herein are kits comprising a small-molecule modulator, a matrix, and instructions describing a method for use according to any of the embodiments described herein. Also provided herein are kits comprising a carboxylate compound, a matrix, and instructions describing a method for use according to any of the embodiments described herein. In some embodiments, the kit may contain any of the compositions or combinations described herein. In some embodiments, the kit contains the compositions or combinations in a concentrated form. In some embodiments, the kit contains the compositions or combinations in solid form. In some embodiments, the kit contains the compositions or combinations in solution form. In some embodiments, the kit additionally contains solutions for dissolving or diluting the compositions and combinations prior to use. In some embodiments, the kit may additionally comprise solutions such as nucleic acid binding solutions, wash buffers, or elution solutions. Selected compositions including articles of manufacture thereof can also be provided as kits. Exemplary articles of manufacture include containers such as vials, bottles, jars, cans, and tubes.

As used herein and in the appended claims, the singular forms "a," "an," and "the" include plural referents unless the context clearly dictates otherwise. For example, "a" or "an" means "at least one" or "one or more." Thus, reference to "a carboxylate compound" refers to one or more carboxylate compounds, and reference to "the method" includes reference to equivalent steps and methods disclosed herein and/or known to those skilled in the art, and so forth. It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The term "alkyl" refers to saturated aliphatic groups including straight-chain, branched-chain, and cyclic groups having from 1 to 12 carbon atoms. "$C_x$-$C_y$ alkyl" refers to alkyl groups with x to y carbon atoms. For example, "$C_1$-$C_8$ alkyl" refers to alkyl groups with 1 to 8 carbon atoms in the chain. Examples of alkyl groups include, but are not limited to, methyl (Me), ethyl (Et), n-propyl, isopropyl, butyl, isobutyl, sec-butyl, tert-butyl (tBu), pentyl, isopentyl, tert-pentyl, hexyl, and isohexyl.

The term "alkenyl" refers to unsaturated aliphatic groups including straight-chain, branched-chain, and cyclic groups having from 2 to 12 carbon atoms and at least one double bond. "$C_x$-$C_y$ alkenyl" refers to alkenyl groups with x to y carbon atoms. For example, "$C_2$-$C_8$ alkenyl" refers to alkenyl groups with 2 to 8 carbon atoms in the chain. Examples of alkenyl groups include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl" refers to unsaturated aliphatic groups including straight-chain, branched-chain, and cyclic groups having from 2 to 12 carbon atoms and at least one triple bond. "$C_x$-$C_y$ alkynyl" refers to alkynyl groups with x to y carbon atoms. For example, "$C_2$-$C_8$ alkynyl" refers to alkynyl groups with 2 to 8 carbon atoms in the chain. Examples of alkynyl groups include, but are not limited to, ethynyl, 1-propynyl, 1-butynyl, 2-butynyl, and 1-methyl-2-butynyl.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

As used herein, the term "binding" and cognates thereof refers to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. For example, proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "contacting" describes any suitable method of bringing a first material in contact or physical association with a second material. In some embodiments, the first material can be in contact with two or more materials. In some embodiments, contact between materials can be achieved through placing all materials in a suitable medium, such as a solution.

The term "halogen" represents chlorine, fluorine, bromine, or iodine. The term "halo" represents chloro, fluoro, bromo, or iodo.

The terms "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

The term "metal" refers to alkali metals such as Li, Na or K, alkaline earth metals such as Ca or Mg, metalloids such as Al, as well as lanthanides, actinides, or transition metals.

As used herein, a "sample" can comprise a naturally occurring component, an artificially derived component, and/or a component artificially synthesized, in part or in whole. In some embodiments, the sample is a biological sample. In some embodiments, the sample comprises nucleic acid molecules, which can be from a biological sample or artificially synthesized and/or modified.

The term "biological sample" as used herein, refers to a sample obtained from a biological subject, including samples of biological tissue or fluid origin obtained in vivo or in vitro. Such samples can be, but are not limited to, body fluid (e.g., blood, blood plasma, serum, or urine), organs, tissues, stool, swab samples, and fractions and cells isolated from mammals (e.g., humans). Biological samples also may include sections of the biological sample including tissues (e.g., sectional portions of an organ or tissue). The term "biological sample" may also include extracts from a biological sample, for example, an antigen from a biological fluid (e.g., blood or urine). A biological sample may be of prokaryotic origin (e.g., bacteria, archaea) or eukaryotic origin (e.g., fungi, plants, insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee or human).

EXAMPLES

Example 1: General Protocol for Acetate-Mediated Size Selection of Nucleic Acids The following protocol is for performing size-selection on a 50 µL PCR reaction. Larger volume reactions can be processed by scaling all reagents here proportionally.
Consumables & Reagents:
  Borosilicate glass spin filters (MO BIO catalog #1200-50-SF)
  SwiftMag® Beads
  DNA Bind: 5.2 M guanidine hydrochloride, 30 mM Tris HCl, 8% isopropanol
  Bind Modifier: 7.5 M ammonium acetate
  Wash Buffer: 11.1 mM Tris buffer, pH 7.4-7.9, 1 mM EDTA, 108 mM NaCl, 50% ethanol
  100% ethanol

TABLE 1

Volumes of reagents for size selection reactions.

| | Volumes (µL) of Reagent | | | | |
|---|---|---|---|---|---|
| PCR reaction | 50 | 50 | 50 | 50 | 50 |
| Bind Modifier | 15 | 20 | 25 | 30 | 35 |
| DNA Bind | 170 | 170 | 170 | 170 | 170 |
| Base-pair cut-off obtained | 100 | 200 | 400 | 1650 | 7000 |

Volumes of reagents needed for the size selection reactions are provided in Table 1. The volume of Bind Modifier (e.g., ammonium acetate) is adjusted to achieve different base pair cut-offs.

The above reagents are combined and mixed briefly by repeated pipetting (3-5×). Thereafter, the full volume is loaded onto a borosilicate glass spin filter and incubated for 2 minutes prior to centrifugation. The spin filter is centrifuged for 30 seconds at 10,000×g. The flow through can be retained for further processing if the desired fragment size was negatively selected (i.e., not bound to the filter). For fragments bound to the spin filter, the filter is washed with 300 µL Wash Buffer via 2 minutes of centrifugation at 16,000×g. Bound DNA fragments are then eluted with 50 µL of PCR-grade water or 10 mM Tris, pH 8.0 via centrifugation at 16,000×g for 1 minute.

Example 2: Acetate-Mediated Size Selection of DNA on Borosilicate Glass Spin Filters Fifty microliters of a nucleic acid-containing sample (diluted 1 kb DNA molecular weight ladder) was mixed with 150 µL of DNA binding solution (5.2 M guanidine hydrochloride, 30 mM Tris-HCl, 8% isopropanol) and 25 µL of DNA bind modifier (7.5 M ammonium acetate). A control sample was made by mixing the same amount of DNA ladder and DNA binding solution with 25 µL of PCR water. The reagents were mixed briefly by repeated pipetting (3-5×). Thereafter, the full volume was loaded onto a borosilicate glass spin filter (MO BIO catalog #1200-50-SF) and incubated for 2 minutes prior to centrifugation. The spin filter was centrifuged for 30 seconds at 10,000×g. The filter was then washed with 300 µL of wash buffer (11.1 mM Tris, 1 mM EDTA, 108 mM NaCl, 50% ethanol; pH 7.4-7.9) via 2 minutes of centrifugation at 16,000×g. The bound DNA fragments were eluted with 50 µL of PCR-grade water or 10 mM Tris, pH 8.0 via centrifugation at 16,000×g for 1 minute. The eluents were analyzed by agarose gel electrophoresis.

Figure 1:
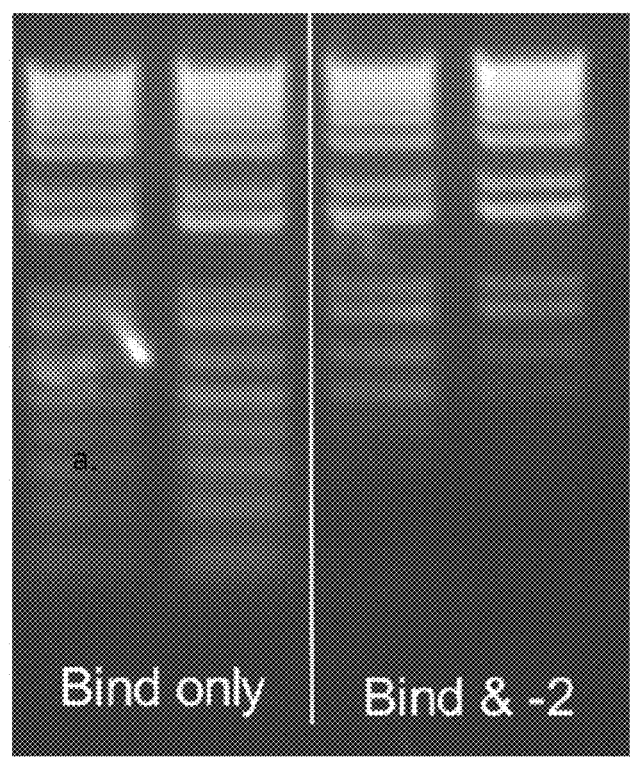
FIG. 1 compares the electrophoretic separation of a 1 kb DNA molecular weight ladder passed through a borosilicate glass spin filter in the absence of a DNA bind modifier (i.e., bands labeled "Bind only") and in the presence of the DNA bind modifier ammonium acetate (i.e., bands labeled "Bind & −2").

FIG. 1 compares the electrophoretic separation of a 1 kb DNA molecular weight ladder passed through a borosilicate glass spin filter in the absence of a DNA bind modifier (i.e., bands labeled "Bind only") and in the presence of the DNA bind modifier ammonium acetate (i.e., bands labeled "Bind & −2"). This shows that the addition of ammonium acetate ("−2") inhibits binding of DNA fragments below a certain molecular weight range (e.g., <400 bp).

Example 3: Effect of Increasing Acetate Concentration on Size Selection of DNA on Borosilicate Glass Spin Fibers Fifty microliters of a nucleic acid-containing sample (diluted 1 kb DNA molecular weight ladder) was mixed with varying volumes of DNA binding solution (5.2 M guanidine hydrochloride, 30 mM Tris-HCl, 8% isopropanol) and DNA bind modifier (7.5 M ammonium acetate). The reagents were mixed briefly by repeated pipetting (3-5×). Thereafter, the full volume was loaded onto a borosilicate glass spin filter (MO BIO catalog #1200-50-SF) and incubated for 2 minutes prior to centrifugation. The spin filter was centrifuged for 30 seconds at 10,000×g. The filter was then washed with 300 µL of wash buffer (11.1 mM Tris, 1 mM EDTA, 108 mM NaCl, 50% ethanol; pH 7.4-7.9) via 2 minutes of centrifugation at 16,000×g. The bound DNA fragments were eluted with 50 µL of PCR-grade water or 10 mM Tris, pH 8.0 via centrifugation at 16,000×g for 1 minute. The eluents were analyzed by agarose gel electrophoresis.

Figure 2:
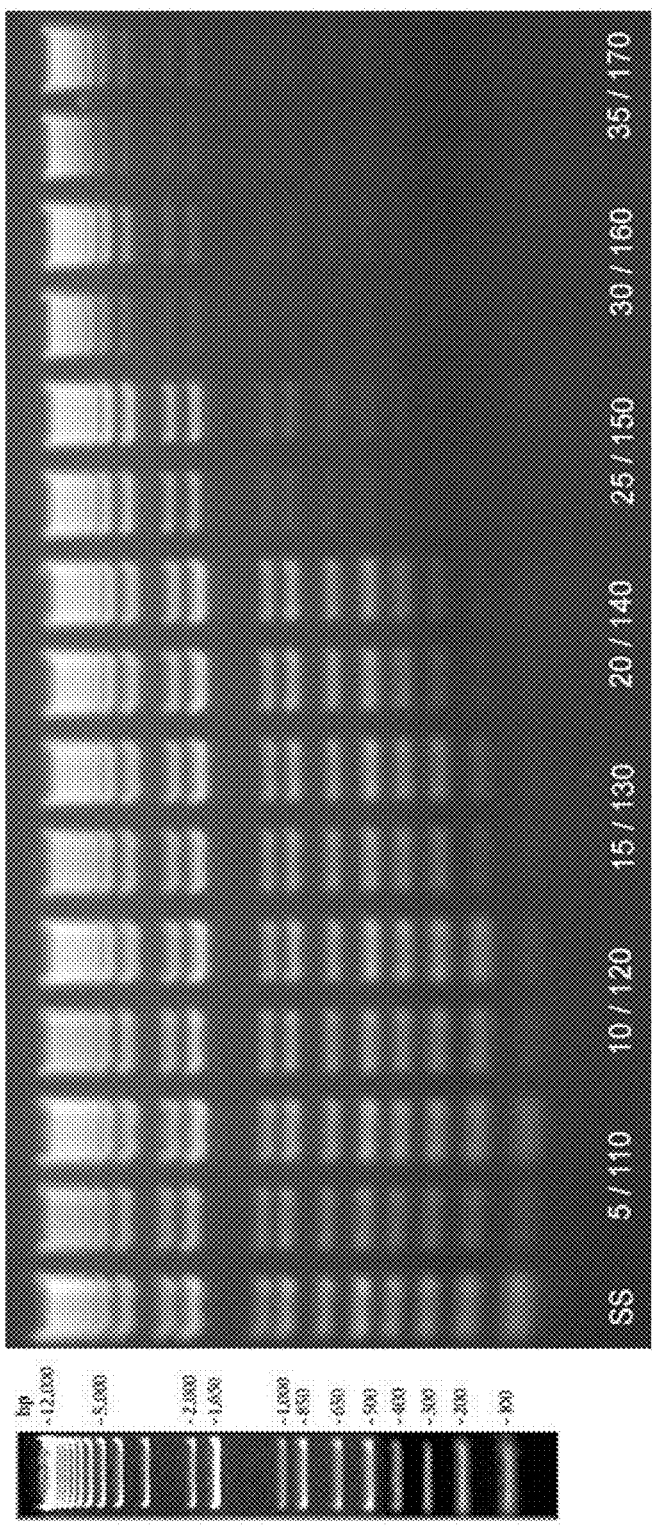
FIG. 2 compares the electrophoretic separation of a 1 kb DNA molecular weight ladder subjected to an increasing amount of ammonium acetate during the binding reaction using borosilicate glass spin filters. The various ratios displayed on the gel (e.g., 5/110, 10/120) correspond to the volume (μL) of 7.5 M ammonium acetate to the volume (μL) of DNA binding buffer (5.2 M guanidine hydrochloride, 30 mM Tris-HCl, 8% isopropanol).

FIG. 2 compares the electrophoretic separation of a 1 kb DNA molecular weight ladder subjected to an increasing amount of ammonium acetate during the binding reaction using borosilicate glass spin filters. The various ratios displayed on the gel (e.g., 5/110, 10/120) correspond to the volume (µL) of 7.5 M ammonium acetate to the volume (µL) of DNA binding solution (5.2 M Guanidine hydrochloride, 30 mM Tris-HCl, 8% isopropanol). The results of this experiment shows that increasing the amount of acetate during the binding reaction leads to an increased molecular weight cut-off of the nucleic acid molecules that bind to the borosilicate glass spin filters. A similar trend is observed when the volume of the nucleic acid binding buffer is held constant and only the ammonium acetate volume is changed (data not shown).

Figure 3:
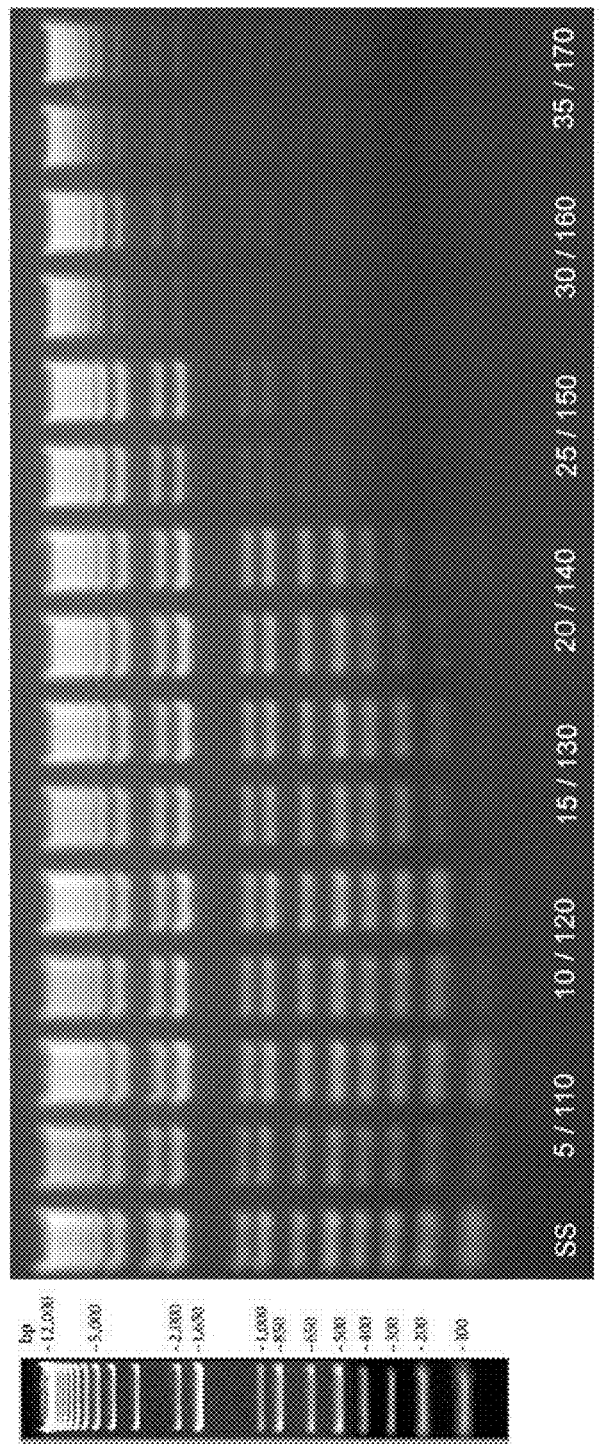
FIG. 3 compares the electrophoretic separation of 1 kb DNA molecular weight ladder samples subjected to an increasing amount of ammonium acetate during the binding reaction using borosilicate glass spin filters. In this gel, the nucleic acid binding solution was held constant at 170 μL while ammonium acetate volumes were varied from 0 to 35 μL.

FIG. 3 compares the electrophoretic separation of a 1 kb DNA molecular weight ladder subjected to an increasing amount of ammonium acetate during the binding reaction using borosilicate glass spin filters. In this gel, the nucleic acid binding solution was held constant at 170 µL while ammonium acetate volumes were varied from 0 to 35 µL. The results of this experiment show that increasing the amount of acetate during the binding reaction leads to an increased molecular weight cut-off of the nucleic acid molecules that bind to the borosilicate glass spin filters.

Example 4: Acetate-Mediated Size Selection of DNA on Silica-Coated Magnetic Beads The same procedures performed above with borosilicate glass spin filters were directly adapted to silica-coated (SwiftMag®) beads without modification. Fifty microliters of a nucleic acid-containing sample (e.g., diluted 1 kb DNA molecular weight ladder) was mixed with varying volumes of DNA bind modifier (e.g., ammonium acetate) and DNA binding solution (e.g., 5.2 M Guanidine hydrochloride, 30 mM Tris-HCl, 8% isopropanol). To the mixture was added 25 μL of SwiftMag® beads, and the sample was mixed with gentle vortexing or orbital mixing for 2 minutes. The reaction was placed on an appropriate magnet to collect the SwiftMag® beads for 2 minutes. The collected beads were washed with 500 μL of Wash Buffer and allowed to air dry for 5 minutes before being suspended in 50 μL of PCR-grade water (eluent) and incubated for 5 minutes with vortexing or orbital mixing. The eluent was analyzed by agarose gel electrophoresis.

Figure 4:
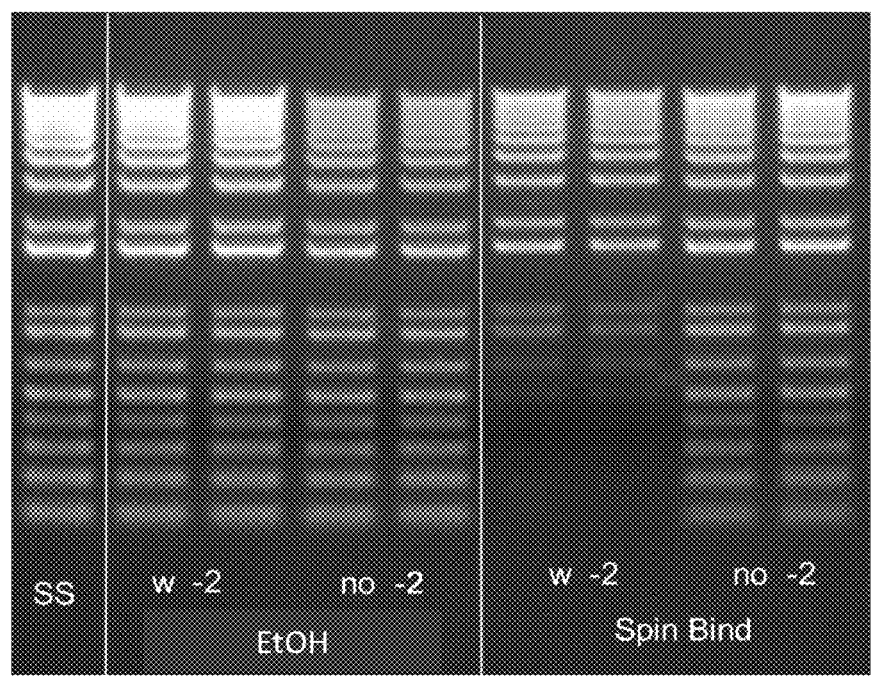
FIG. 4 compares electrophoretic separation of 1 kb DNA molecular weight ladder samples contacted with silica-coated magnetic beads (SwiftMag® beads) in the presence or absence of ammonium acetate and in the presence or absence of DNA binding solution ("Spin Bind"). In the panel labeled "EtOH", Spin Bind was substituted with an equal volume of 100% ethanol, with or without ammonium acetate ("−2"). In the right panel ("Spin Bind"), DNA binding solution (5.2 M guanidine hydrochloride, 30 mM Tris HCl, 8% isopropanol) was used with or without ammonium acetate. 50 μL of DNA ladder was combined with 200 μL DNA Binding Solution (or ethanol) and 25 μL ammonium acetate.

FIG. 4 compares electrophoretic separation of a 1 kb DNA molecular weight ladder samples contacted with silica-coated magnetic beads (SwiftMag® beads) in the presence or absence of ammonium acetate and in the presence of absence of DNA binding solution ("Spin Bind"). In the panel labeled "EtOH", Spin Bind was substituted with an equal volume of 100% ethanol, with or without ammonium acetate ("−2"). In the right panel ("Spin Bind"), DNA binding solution (5.2 M guanidine hydrochloride, 30 mM Tris HCl, 8% isopropanol) was used with or without ammonium acetate. 50 μL of DNA ladder was combined with 200 μL DNA Binding Solution (or ethanol) and 25 μL ammonium acetate. The results of this experiment indicate that the combination of Spin Bind and ammonium acetate resulted in nucleic acid size selection.

Figure 5:
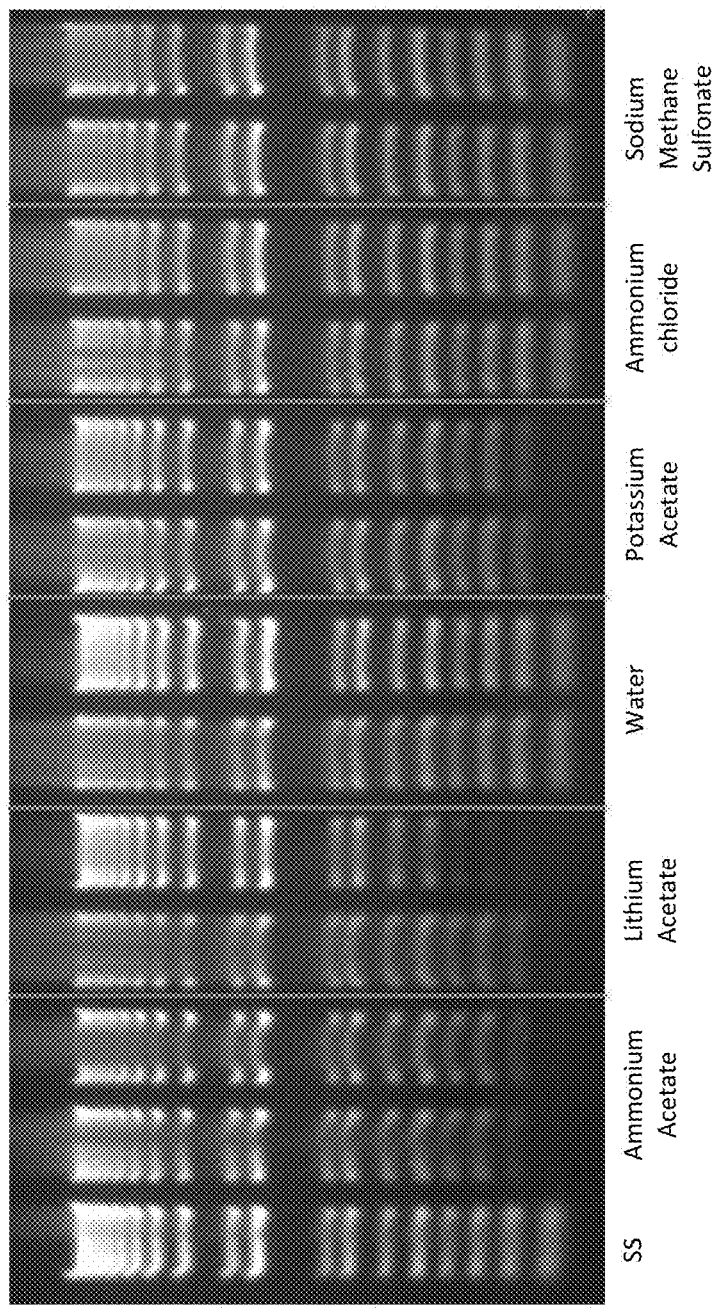
FIG. 5 compares the electrophoretic separation of 1 kb DNA molecular weight ladder samples contacted with silica-coated magnetic beads in the presence of different DNA bind modifiers. Ammonium acetate, lithium acetate, water, potassium acetate, ammonium chloride, and sodium methane sulfonate were used as DNA bind modifiers. 50 μL of DNA ladder was combined with 200 μL of DNA Binding Solution and 25 μL of the above compounds.

FIG. 5 compares the electrophoretic separation of 1 kb DNA molecular weight ladder samples contacted with silica-coated magnetic beads in the presence of different DNA bind modifiers. Ammonium acetate, lithium acetate, water, potassium acetate, ammonium chloride, and sodium methane sulfonate were used as DNA bind modifiers. 50 μL of DNA ladder was combined with 200 μL of DNA Binding Solution and 25 μL of the above compounds. Size selection was observed for all acetates, regardless of the cation ($NH_4^+$, $Li^+$, $K^+$). In contrast, removal of the acetate and retention of the ammonium cation, for example, did not result in observable size selection.

Example 5: Double-Sided Acetate-Mediated Size Selection of Nucleic Acids Using Borosilicate Glass Fiber Matrix An example of double-sided selection is given below. In this example, the double-sided selection of a 50 μL PCR reaction is carried out to isolate DNA fragments between 400 and 1650 base pairs.
Bind Fragments>1650 bp:
To a solution of 150 μL of DNA Bind and 25 μL of Bind Modifier (e.g., ammonium acetate) is added 50 μL of a PCR sample. The full volume of the solution mixture is loaded onto a borosilicate glass spin filter and incubated 2 minutes prior to centrifugation. The spin filter is centrifuged for 30 seconds at 10,000×g, and the filtrate (containing fragments<1650 bp) is collected for further processing. The spin filter (containing fragments>1650 bp) is discarded.
Bind Fragments≥400 bp<1650 bp:
An equal volume of 100% ethanol is added to the filtrate from the step above, and this solution is applied to a fresh spin filter. The sample is centrifuged for 30 seconds at 10,000×g, and the filtrate is discarded. The filter is washed with 300 μL Wash Buffer, spun dry and the DNA is eluted with 50 μL of PCR-grade water. Then, 140 μL of DNA Bind and 20 μL of Bind Modifier (i.e., ammonium acetate) are added to the eluted DNA. The entire volume of the mixture is loaded on the same spin filter used in the previous step and centrifuged for 30 seconds at 10,000×g. The filtrate is discarded, and the spin filter is washed with 300 μL Wash Buffer, spun dry and the DNA is eluted with 50 μL of PCR-grade water.

Example 6: Double-Sided Acetate-Mediated Size Selection of Nucleic Acids Using Silica-Coated Magnetic Beads The same procedures performed above with borosilicate glass spin filters are directly adapted to silica-coated (SwiftMag®) beads without modification. In this example, the double-sided selection of a 50 μL PCR reaction is carried out to isolate DNA fragments between 400 and 1650 base pairs:
Bind Fragments>1650 bp:
To a solution of 150 μL of DNA Bind and 25 μL of Bind Modifier (e.g., ammonium acetate) is added 50 μL a PCR sample. To the mixture is added 25 μL of SwiftMag® beads, and the sample is mixed with gentle vortexing or orbital mixing for 2 minutes. The reaction is placed on an appropriate magnet to collect the SwiftMag® beads for 2 minutes. The supernatant is removed and retained, and the collected beads (containing fragments>1650 bp) are discarded.
Bind Fragments≥400 bp<1650 bp:
An equal volume of 100% ethanol is added to the supernatant and a fresh aliquot of SwiftMag® beads (25 μL). The sample is mixed as above and collected on a magnet for 2 minutes. The supernatant is removed, and the samples are removed from the magnet. The bound DNA is eluted with 50 μL of PCR-grade water. With the SwiftMag® beads still present, 140 μL of DNA Bind and 20 μL of Bind Modifier are added to the eluted DNA, and reaction is mixed for 2 minutes. The reaction is placed on an appropriate magnet to collect the SwiftMag® beads for 2 minutes. The supernatant is removed, and the beads are washed with 500 μL of Wash Buffer. The beads are collected on a magnet, and the supernatant is removed. The beads are allowed to air dry for 5 minutes before being suspended in 50 μL of PCR-grade water and incubated for 5 minutes with vortexing or orbital mixing. The samples are placed back on a magnet for 2 minutes, and the eluent is transferred to the new tubes.

Example 7: Effect of Different Alkali Metal Cation Acetates on Size Selection of DNA on Borosilicate Glass Spin Filters Fifty microliters of a nucleic acid-containing sample (diluted 1 kb DNA molecular weight ladder) was mixed with 170 μL of DNA binding solution and 0-35 μL of each DNA bind modifier. A control sample was made by mixing the same amount of DNA ladder and DNA binding solution without DNA bind modifier. Ammonium acetate, sodium acetate, lithium acetate, cesium acetate, rubidium acetate, and potassium acetate were used as DNA bind modifiers. The full volume of the reagents was loaded onto a borosilicate glass spin filter and incubated for 2 minutes prior to centrifugation. The spin filter was centrifuged for 1 minute at 10,000×g. The filter was then washed with 300 μL of wash buffer via 1 minute of centrifugation at 10,000×g. The spin filter was centrifuged again for 2 minutes at 16,000×g to spin dry. The bound DNA fragments were incubated with 50 μL of elution buffer for 2 minutes and centrifuged at 10,000×g for 1 minute to elute. The eluents were analyzed by agarose gel electrophoresis.

Figure 6A:
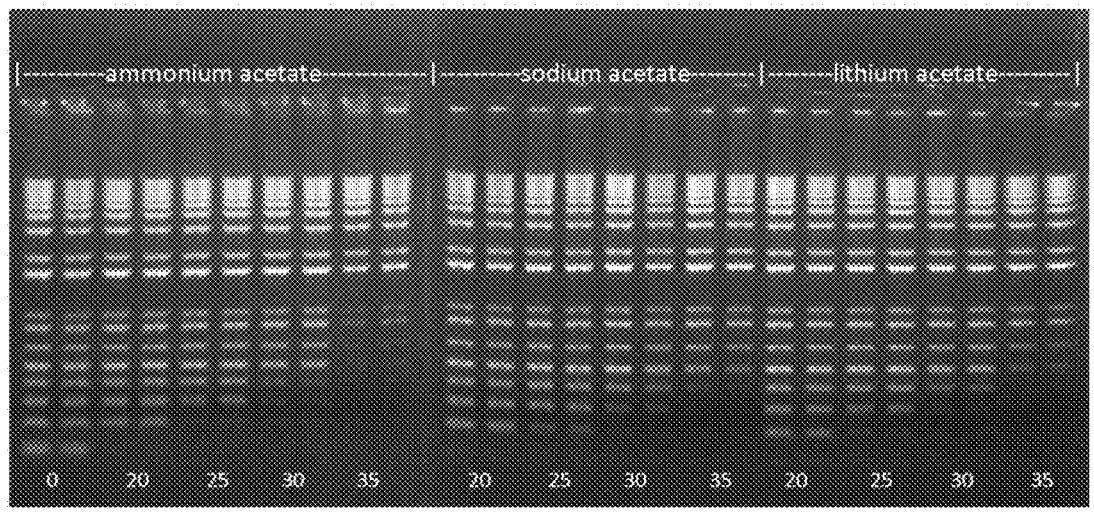
FIG. 6A compares the electrophoretic separation of 1 kb DNA molecular weight ladder samples subjected to increasing amounts of different DNA bind modifiers during the binding reaction using borosilicate glass spin filters. Ammonium acetate, sodium acetate, and lithium acetate were used as DNA bind modifiers. In this gel, the nucleic acid binding solution was held constant at 170 μL while DNA bind modifier volumes were varied from 0 to 35 μL.

FIG. 6A compares the electrophoretic separation of 1 kb DNA molecular weight ladder samples subjected to increasing amounts of different DNA bind modifiers during the binding reaction using borosilicate glass spin filters. Ammonium acetate, sodium acetate, and lithium acetate (0-35 μL) were used as DNA bind modifiers in this gel.

Figure 6B:
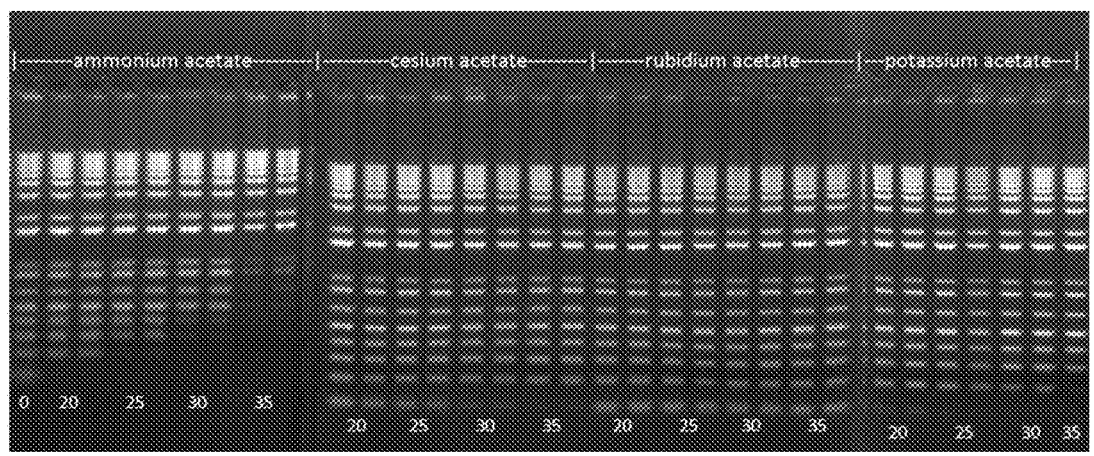
FIG. 6B compares the electrophoretic separation of 1 kb DNA molecular weight ladder samples subjected to increasing amounts of different DNA bind modifiers during the binding reaction using borosilicate glass spin filters. Ammonium acetate, cesium acetate, ribidium acetate, and potassium acetate were used as DNA bind modifiers. In this gel, the nucleic acid binding solution was held constant at 170 μL while DNA bind modifier volumes were varied from 0 to 35 μL.

FIG. 6B compares the electrophoretic separation of 1 kb DNA molecular weight ladder samples subjected to increasing amounts of different DNA bind modifiers during the binding reaction using borosilicate glass spin filters. Ammonium acetate, cesium acetate, ribidium acetate, and potassium acetate (0-35 μL) were used as DNA bind modifiers in this gel.

Example 8: Effect of Different Ammonium Acetates on Size Selection of DNA on Borosilicate Glass Spin Filters Fifty microliters of a nucleic acid-containing sample (diluted 1 kb DNA molecular weight ladder) was mixed with 170 μL of DNA binding solution and 0-35 μL of each DNA bind modifier. A control sample was made by mixing the 50 μL DNA ladder and 170 μL of DNA binding solution without DNA bind modifier. 7.5 M ammonium acetate, 6.3 M tetramethyl ammonium acetate, 3.44 M tetramethyl ammonium acetate tetrahydrate, 3.12 M tetramethyl ammonium acetate, 4.67 M tetramethyl ammonium acetate, and 6.23 M tetramethyl ammonium acetate were used as DNA bind modifiers. The full volume of the reagents was loaded onto a borosilicate glass spin filter and incubated for 2 minutes prior to centrifugation. The spin filter was centrifuged for 1 minute at 10,000×g. The filter was then washed with 500 μL of wash buffer via 1 minute of centrifugation at 10,000×g. The spin filter was centrifuged again for 2 minutes at 16,000×g to spin dry. The bound DNA fragments were incubated with 50 μL of elution buffer for 2 minutes and centrifuged at 10,000×g for 1 minute to elute. The eluents were analyzed by agarose gel electrophoresis.

Figure 7A:
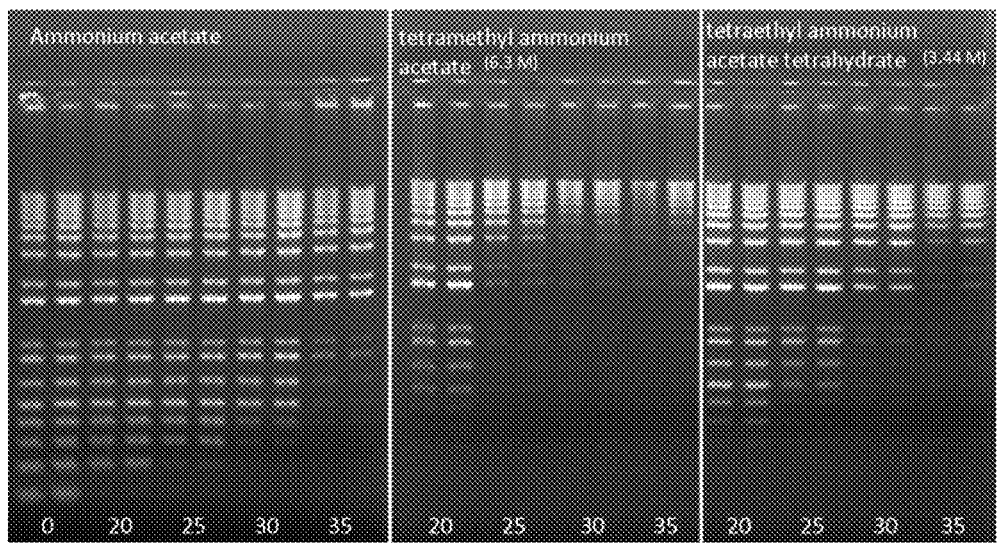
FIG. 7A compares the electrophoretic separation of 1 kb DNA molecular weight ladder samples subjected to increasing amounts of different DNA bind modifiers during the binding reaction using borosilicate glass spin filters. 7.5 M Ammonium acetate, 6.3 M tetramethyl ammonium acetate, and 3.44 M tetramethyl ammonium acetate tetrahydrate were used as DNA bind modifiers. In this gel, the nucleic acid binding solution was held constant at 170 μL while DNA bind modifier volumes were varied from 0 to 35 μL.

FIG. 7A compares the electrophoretic separation of 1 kb DNA molecular weight ladder samples subjected to increasing amounts of different DNA bind modifiers during the binding reaction using borosilicate glass spin filters. 7.5 M ammonium acetate, 6.3 M tetramethyl ammonium acetate, and 3.44 M tetramethyl ammonium acetate tetrahydrate were used as DNA bind modifiers in this gel.

Figure 7B:
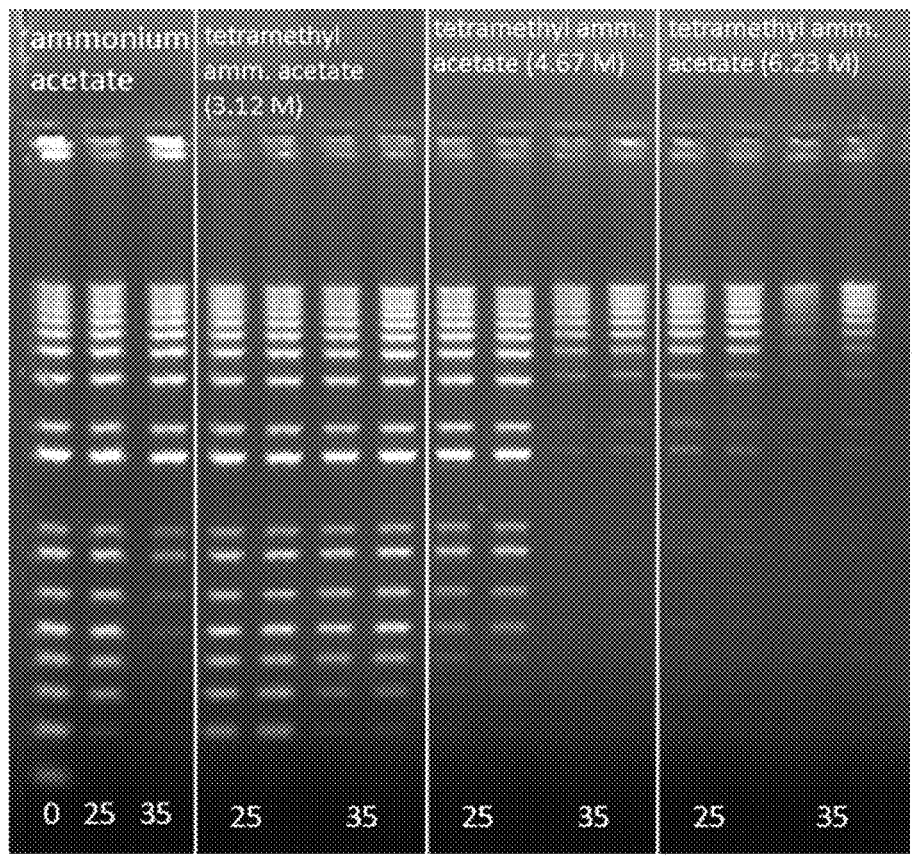
FIG. 7B compares the electrophoretic separation of 1 kb DNA molecular weight ladder samples subjected to increasing amounts of different DNA bind modifiers during the binding reaction using borosilicate glass spin filters. 7.5 M Ammonium acetate, 3.12 M tetramethyl ammonium acetate, 4.67 M tetramethyl ammonium acetate, and 6.23 M tetramethyl ammonium acetate were used as DNA bind modifiers. In this gel, the nucleic acid binding solution was held constant at 170 μL while DNA bind modifier volumes were 0, 25, and 35 μL.

FIG. 7B compares the electrophoretic separation of 1 kb DNA molecular weight ladder samples subjected to increasing amounts of different DNA bind modifiers during the binding reaction using borosilicate glass spin filters. 7.5 M ammonium acetate, 3.12 M tetramethyl ammonium acetate, 4.67 M tetramethyl ammonium acetate, and 6.23 M tetramethyl ammonium acetate were used as DNA bind modifiers in this gel. In this gel, the nucleic acid binding solution was held constant at 170 μL while DNA bind modifier volumes were 0, 25 and 35 μL.

Example 9: Effect of Different Ammonium Anions on Size Selection of DNA on Borosilicate Glass Spin Filters Fifty microliters of a nucleic acid-containing sample (diluted 1 kb DNA molecular weight ladder) was mixed with 170 μL of DNA binding solution and 35 μL of each DNA bind modifier. A control sample was made by mixing the 50 μL DNA ladder and 170 μL of DNA binding solution without DNA bind modifier. Tetramethyl ammonium acetate (4.7 M), ammonium phosphate dibasic (4.03 M), choline chloride (5.68 M), Tris(2-hydroxyethyl)methylammonium methylsulfate (TMAMS), ammonium sulfate, 2.02 M diammonium phosphate (DAP), and 2.42 M DAP were used as DNA bind modifiers. The full volume of the reagents was loaded onto a borosilicate glass spin filter and incubated for 2 minutes prior to centrifugation. The spin filter was centrifuged for 1 minute at 10,000×g. The filter was then washed with 500 μL of wash buffer via 1 minute of centrifugation at 10,000×g. The spin filter was centrifuged again for 2 minutes at 16,000×g to spin dry. The bound DNA fragments were incubated with 50 μL of elution buffer for 2 minutes and centrifuged at 10,000×g for 1 minute to elute. The eluents were analyzed by agarose gel electrophoresis.

Figure 8A:
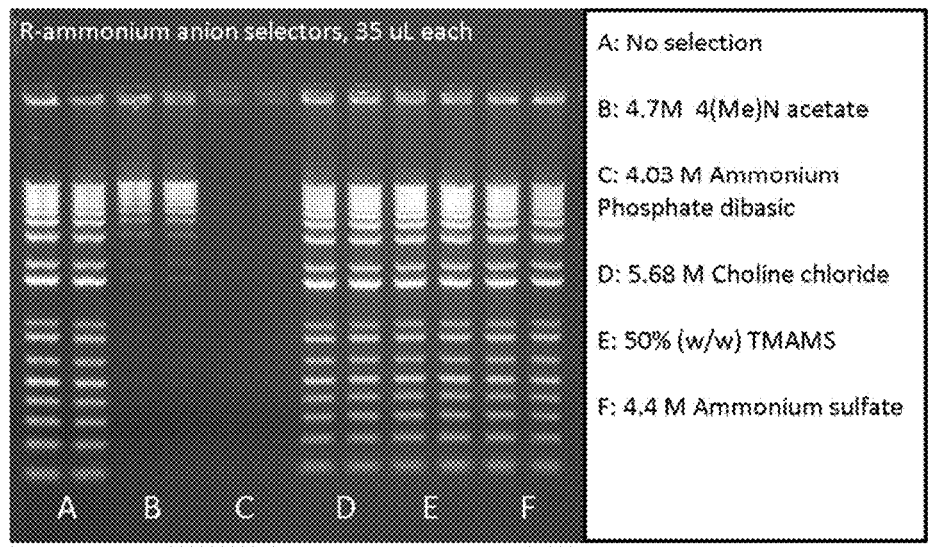
FIG. 8A compares the electrophoretic separation of 1 kb DNA molecular weight ladder samples in the presence or absence of different DNA bind modifiers during the binding reaction using borosilicate glass spin filters. Sample A contains the 1 kb DNA molecular weight ladder sample in the absence of any DNA bind modifiers. Tetramethyl ammonium acetate (4.7 M), ammonium phosphate dibasic (4.03 M), choline chloride (5.68 M), Tris(2-hydroxyethyl)methylammonium methylsulfate (TMAMS), and ammonium sulfate (4.4 M) were used as DNA bind modifiers. 50 μL of DNA ladder was combined with 170 μL of nucleic acid binding solution and 35 μL of the above compounds.

FIG. 8A compares the electrophoretic separation of 1 kb DNA molecular weight ladder samples in the presence or absence of different DNA bind modifiers during the binding reaction using borosilicate glass spin filters. Sample A contained 1 kb DNA molecular weight ladder sample in the absence of any DNA bind modifiers. Tetramethyl ammonium acetate (4.7 M), ammonium phosphate dibasic (4.03 M), choline chloride (5.68 M), Tris(2-hydroxyethyl)methylammonium methylsulfate (TMAMS), and ammonium sulfate were used as DNA bind modifiers (4.4 M) in this gel.

Figure 8B:
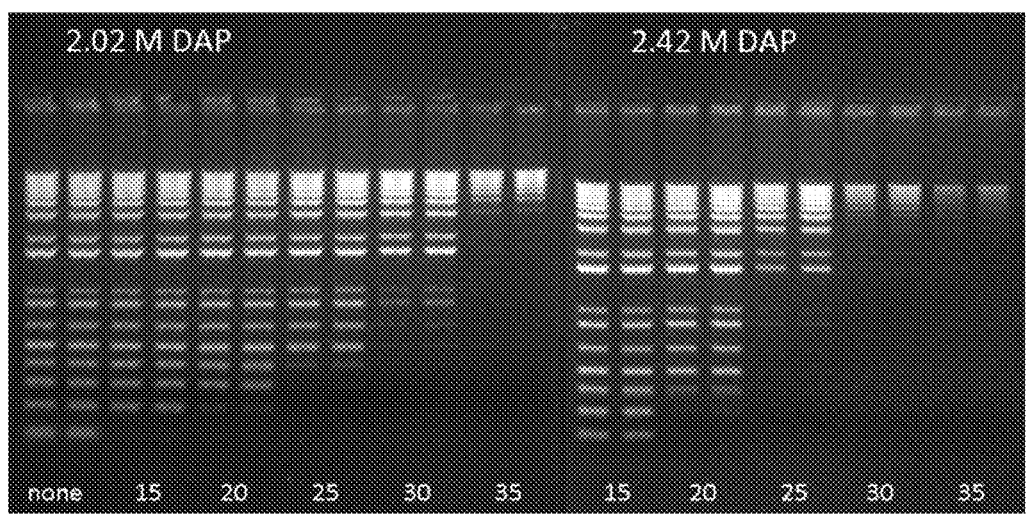
FIG. 8B compares the electrophoretic separation of 1 kb DNA molecular weight ladder samples in the presence of increasing amounts of diammonium phosphate (DAP) during the binding reaction using borosilicate glass spin filters. 2.02 M DAP and 2.42 M DAP were used as DNA bind modifiers. 50 μL of DNA ladder was combined with 170 μL of nucleic acid binding solution and DAP volumes were varied from 0 to 35 μL.

FIG. 8B compares the electrophoretic separation of 1 kb DNA molecular weight ladder samples in the presence of increasing amounts of DAP during the binding reaction using borosilicate glass spin filters. In this gel, 2.02 M DAP and 2.42 M DAP were used as DNA bind modifiers.

Figure 8C:
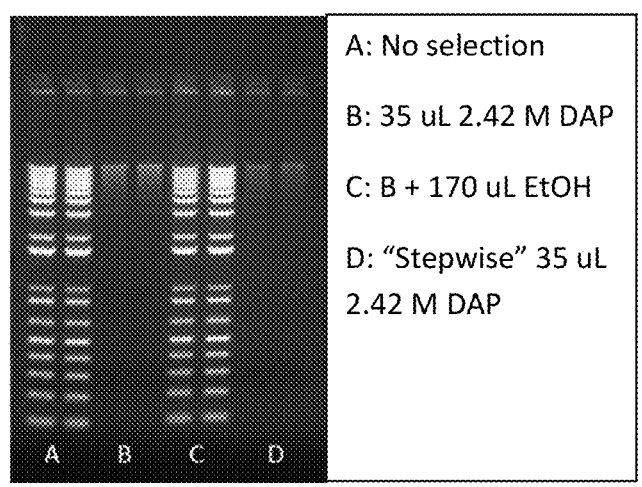
FIG. 8C compares the electrophoretic separation of 1 kb DNA molecular weight ladder samples in the presence or absence of diammonium phosphate (DAP) during the binding reaction using borosilicate glass spin filters subject to selection and different stages. 2.42 M DAP was used as DNA bind modifier in samples B, C, and D. Sample A contained the 1 kb DNA molecular weight ladder sample in the absence of any DNA bind modifiers. Samples B was 1 kb DNA molecular weight ladder passed through a borosilicate glass spin filter in the presence of 35 μL of 2.42 M DAP. Sample C was the recovered flow through of 1 kb DNA molecular weight ladder passed through a borosilicate glass spin filter in the presence of 35 μL of 2.42 M DAP mixed with ethanol. Sample D contained the 1 kb DNA molecular weight ladder sample in the absence of any DNA bind modifiers bound to the filter that was then subjected to selection with 35 μL of 2.42 M DAP ('on-filter selection').

FIG. 8C compares the electrophoretic separation of 1 kb DNA molecular weight ladder samples in the presence or absence of diammonium phosphate (DAP) during the binding reaction using borosilicate glass spin filters subject to selection and different stages. 2.42 M DAP was used as DNA bind modifier in samples B, C, and D. Sample A contained the 1 kb DNA molecular weight ladder sample in the absence of any DNA bind modifiers. Samples B was 1 kb DNA molecular weight ladder passed through a borosilicate glass spin filter in the presence of 35 μL of 2.42 M DAP. Sample C was the recovered flow through of 1 kb DNA molecular weight ladder passed through a borosilicate glass spin filter in the presence of 35 μL of 2.42 M DAP mixed with ethanol. Sample D contained the 1 kb DNA molecular weight ladder sample in the absence of any DNA bind modifiers bound to the filter that was then subjected to selection with 35 μL of 2.42 M DAP ('on-filter selection').

Example 10: Double-Sided Acetate-Mediated Size Selection of Nucleic Acids Using Borosilicate Glass Filters In cases where target DNA fragments were mixed with both larger and smaller DNA fragments, the target DNA fragments in the middle range were isolated with a double sided approach involving a two-step process. For control, Sample A contained 50 μL of a nucleic acid-containing sample (diluted 1 kb DNA molecular weight ladder) mixed with 170 μL of DNA binding solution and no Bind Modifier. The sample was centrifuged for 1 minute at 10,000×g, and the filtrate discarded. The filter was washed with 500 μL wash buffer and centrifuged at 10,000×g for 1 minute. The column was then spun dry via centrifugation at 16,000×g for 2 minutes. The bound DNA fragments were incubated with 50 μL of elution buffer for 2 minutes and centrifuged at 10,000×g for 1 minute to elute. The eluents were analyzed by agarose gel electrophoresis.

Bind Fragments Larger than the Target Range in Primary Spin Column:

Samples B and C were 1 kb DNA molecular weight ladder passed through a borosilicate glass spin filter in the presence of 35 μL and 25 respectively, of 4.7 M tetramethyl ammonium acetate. The sample was centrifuged for 1 minute at 10,000×g, and the filtrate discarded. The filter was washed with 500 μL wash buffer and centrifuged at 10,000×g for 1 minute. The column was then spun dry via centrifugation at 16,000×g for 2 minutes. The bound DNA fragments were incubated with 50 μL of elution buffer for 2 minutes and centrifuged at 10,000×g for 1 minute to elute. The eluents were analyzed by agarose gel electrophoresis. Sample D was the recovered flow through of 1 kb DNA molecular weight ladder that passed through a borosilicate glass spin filter in the presence of 35 μL of 4.7 M tetramethyl ammonium acetate with a single volume of ethanol added. This sample was added to a new spin column and centrifuged for 1 minute at 10,000×g. The filter was washed with 500 wash buffer and centrifuged at 10,000×g for 1 minute. The column was then spun dry via centrifugation at 16,000×g for 2 minutes. The bound DNA fragments were incubated with 50 of elution buffer for 2 minutes and centrifuged at 10,000×g for 1 minute to elute. The eluents were analyzed by agarose gel electrophoresis.

Sample E was subjected to two selection steps. In the first selection step, 400 μL of a nucleic acid-containing sample (diluted 1 kb DNA molecular weight ladder) was mixed with 680 of DNA binding solution and 140 μL Bind Modifier (e.g., 4.7 M tetramethyl ammonium acetate). 305 μL of the solution mixture was loaded onto a borosilicate glass spin filter and incubated 2 minutes prior to centrifugation. The spin filter was centrifuged for 1 minute at 10,000×g, and the filtrate (containing fragments smaller than the target) was collected for further processing. The spin filter (containing fragments larger than the target) was discarded.

Remove Fragments Smaller than the Target Range in Secondary Spin Column:

For the second selection step of Sample E, an equal volume of 100% ethanol was added to the filtrate collected from the step above, and this solution was applied to a fresh spin filter. The sample was centrifuged for 1 minute at 10,000×g, and the filtrate discarded. A mixture of 25 μL 4.7 M tetramethyl ammonium acetate and 170 μL of DNA binding solution was added to the filter. The sample was then centrifuged for 1 minute at 10,000×g and the filtrate discarded. The filter was washed with 500 μL wash buffer and centrifuged at 10,000×g for 1 minute. The column was then spun dry via centrifugation at 16,000×g for 2 minutes. The bound DNA fragments were incubated with 50 μL of elution buffer for 2 minutes and centrifuged at 10,000×g for 1 minute to elute. The eluents were analyzed by agarose gel electrophoresis.

Figure 9A:
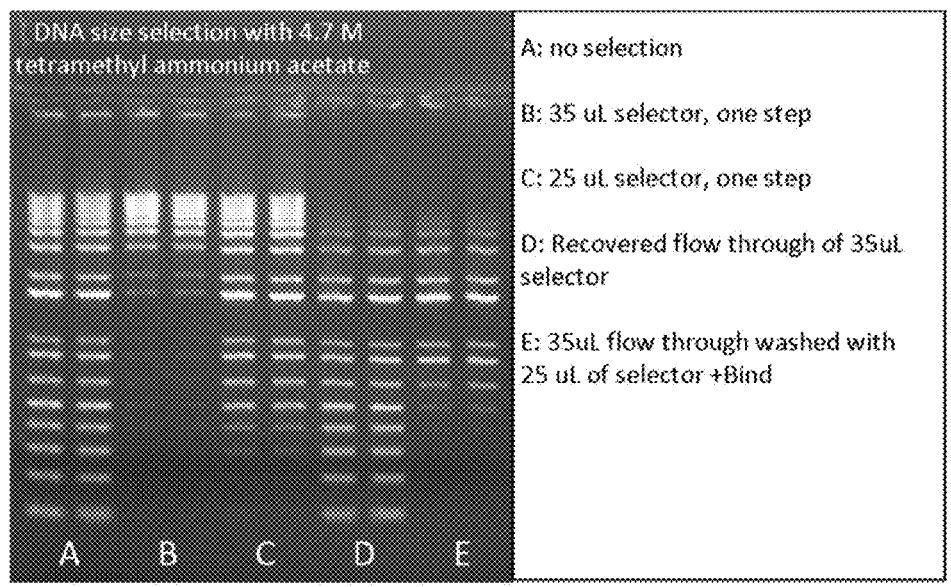
FIG. 9A compares the electrophoretic separation of 1 kb DNA molecular weight ladder samples in the presence or absence of DNA bind modifiers during the binding reaction using borosilicate glass spin filters subject to one or more steps of selection. Sample A contained the 1 kb DNA molecular weight ladder sample in the absence of any DNA bind modifiers. In samples B, C, D, and E, 4.7 M tetramethyl ammonium acetate was used as DNA bind modifier. Samples B and C were 1 kb DNA molecular weight ladder passed through a borosilicate glass spin filter in the presence of 35 μL and 25 μL, respectively, of 4.7 M tetramethyl ammonium acetate. Sample D was the recovered flow through of 1 kb DNA molecular weight ladder passed through a borosilicate glass spin filter in the presence of 35 of 4.7 M tetramethyl ammonium acetate (Sample B); the flow through was bound to a spin filter with ethanol, washed and eluted. Sample E was the flow through of 1 kb DNA molecular weight ladder passed through a borosilicate glass spin filter in the presence of 35 μL of 4.7 M tetramethyl ammonium acetate; the collected flow through was bound to a spin filter with ethanol, as in Sample D, and subjected to a second step of selection with 25 μL of 4.7 M tetramethyl ammonium acetate.

FIG. 9A compares the electrophoretic separation of 1 kb DNA molecular weight ladder samples in the presence or absence of DNA bind modifiers during the binding reaction using borosilicate glass spin filters subject to one or more steps of selection. Sample A contained the 1 kb DNA molecular weight ladder sample in the absence of any DNA bind modifiers. In samples B, C, D, and E, 4.7 M tetramethyl ammonium acetate was used as DNA bind modifier. Samples B and C were 1 kb DNA molecular weight ladder passed through a borosilicate glass spin filter in the presence of 35 μL and 25 respectively, of 4.7 M tetramethyl ammonium acetate. Sample D was the recovered flow through of 1 kb DNA molecular weight ladder passed through a borosilicate glass spin filter in the presence of 35 of 4.7 M tetramethyl ammonium acetate (Sample B); the flow through was bound to a spin filter with ethanol, washed and eluted. Sample E was the flow through of 1 kb DNA molecular weight ladder passed through a borosilicate glass spin filter in the presence of 35 μL of 4.7 M tetramethyl ammonium acetate; the collected flow through was bound to a spin filter with ethanol, as in Sample D, and subjected to a second step of selection with 25 μL of 4.7 M tetramethyl ammonium acetate.

Example 11: Double-Sided Acetate-Mediated Size Selection of Nucleic Acids Using Silica-Coated Magnetic Beads In cases where target DNA fragments were mixed with both larger and smaller DNA fragments, the target DNA fragments in the middle range was isolated with a double sided approach involving a two-step process using silica-coated (SwiftMag®) beads. For control, Sample A contained 50 μL of a nucleic acid-containing sample (diluted 1 kb DNA molecular weight ladder) mixed with 170 μL of DNA binding solution, no Bind Modifier, and 25 μL of SwiftMag® beads. The sample was mixed by vortexing every 2 minutes for 10 minutes, then placed on an appropriate magnet to collect the SwiftMag® beads for 2 minutes. The supernatant was removed, and the beads were washed with 500 μL of Wash Buffer. The beads were collected on a magnet, and the supernatant was removed. The beads were incubated with lids open for 20 minutes on the magnetic rack before being suspended in 50 μL of elution buffer water and mixed by vortexing every 2 minutes for 10 minutes. The samples were placed back on a magnet and the eluent was transferred to the new tubes. The eluents were analyzed by agarose gel electrophoresis.

Bind Fragments Larger than the Target Range in Primary Spin Column:

Samples B and C were 1 kb DNA molecular weight ladder contacted with silica-coated magnetic beads in the presence 20 μL and 25 μL, respectively, of 4.7 M tetramethyl ammonium acetate. The supernatant was removed, and the beads were washed with 500 μL of Wash Buffer. The beads were collected on a magnet, and the supernatant was removed. The beads were incubated with lids open for 20 minutes on the magnetic rack before being suspended in 50 μL of elution buffer water and mixed by vortexing every 2 minutes for 10 minutes. The samples were placed back on a magnet and the eluent was transferred to the new tubes. The eluents were analyzed by agarose gel electrophoresis. Sample D was the recovered supernatant of 1 kb DNA molecular weight ladder contacted with silica-coated magnetic beads in the presence of 25 μL of 4.7 M tetramethyl ammonium acetate. The supernatant was transferred to a clean tube, 245 μL ethanol and 25 μL of SwiftMag® beads was added to this tube. The sample was mixed by vortexing every 2 minutes for 10 minutes, then placed on an appropriate magnet to collect the SwiftMag® beads for 2 minutes. The supernatant was then removed, and the beads were washed with 500 μL of Wash Buffer. The beads were collected on a magnet, and the supernatant was removed. The beads were incubated with lids open for 20 minutes on the magnetic rack before being suspended in 50 μL of elution buffer water and mixed by vortexing every 2 minutes for 10 minutes. This sample was placed back on a magnet and the eluent was transferred to the new tubes. The eluents were analyzed by agarose gel electrophoresis.

Sample E was subjected to two selection steps. In the first selection step, 50 μL of a nucleic acid-containing sample (diluted 1 kb DNA molecular weight ladder) was mixed with 170 μL of DNA binding solution and 25 μL Bind Modifier (4.7 M tetramethyl ammonium acetate). To the mixture, 25 μL of SwiftMag® beads was added, and the sample was mixed by vortexing every 2 minutes for 10 minutes. The reaction was placed on an appropriate magnet to collect the SwiftMag® beads for 2 minutes. The supernatant was removed and retained, and the collected beads (containing fragments larger than the target) were discarded.

Remove Fragments Smaller than the Target Range in Secondary Spin Column:

In the second selection step of Sample E, 245 µL of 100% ethanol and a fresh aliquot of SwiftMag® beads (25 µL) was added to the supernatant. The sample was mixed by vortexing every 2 minutes for 10 minutes and collected on a magnet for 2 minutes. The supernatant was removed, and the samples were removed from the magnet. With the SwiftMag® beads still present, 50 µL of water, 170 µL of DNA binding solution, and 20 µL of 4.7 M tetramethyl ammonium acetate were added to the pellet, and reaction was mixed by vortexing every 2 minutes for 10 minutes. The reaction was placed on an appropriate magnet to collect the SwiftMag® beads for 2 minutes. The supernatant was removed, and the beads were washed with 500 µL of Wash Buffer. The beads were collected on a magnet, and the supernatant was removed. The beads were incubated with lids open for 20 minutes on the magnetic rack before being suspended in 50 µL of elution buffer water and mixed by vortexing every 2 minutes for 10 minutes. The samples were placed back on a magnet and the eluent was transferred to the new tubes. The eluents were analyzed by agarose gel electrophoresis.

Figure 9B:
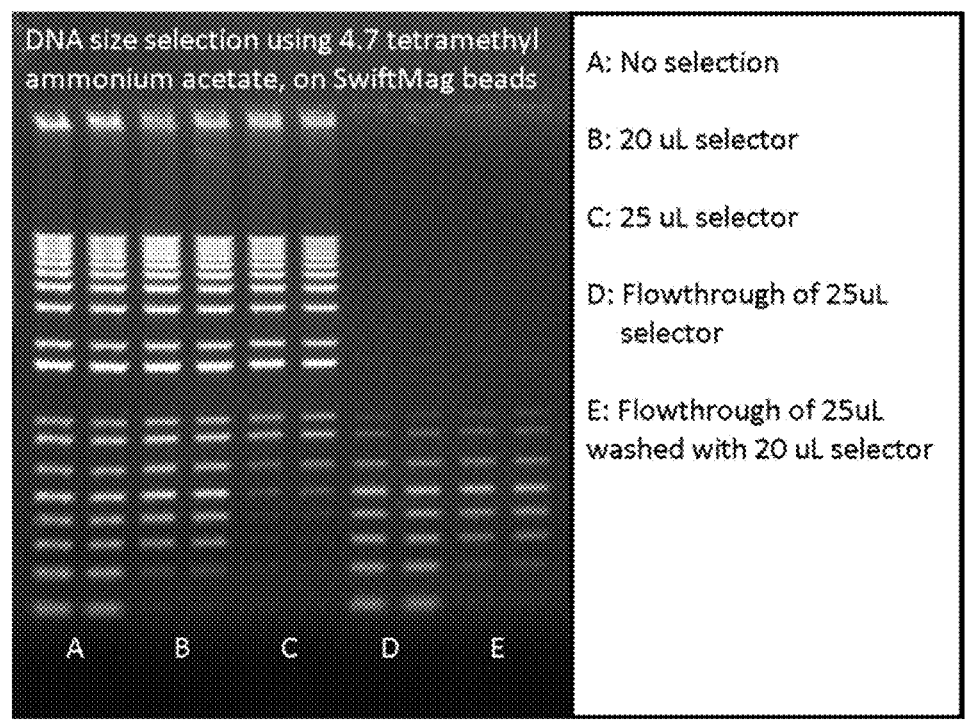
FIG. 9B compares electrophoretic separation of 1 kb DNA molecular weight ladder samples contacted with silica-coated magnetic beads (SwiftMag® beads) in the presence or absence of 4.7 M tetramethyl ammonium acetate subject to one or more steps of selection. Tetramethyl ammonium acetate at 4.7 M was used as DNA bind modifier in samples B, C, D, and E. Samples B and C were 1 kb DNA molecular weight ladder contacted with silica-coated magnetic beads in the presence of 20 μL and 25 respectively, of 4.7 M tetramethyl ammonium acetate. Sample D was the recovered supernatant of 1 kb DNA molecular weight ladder contacted with silica-coated magnetic beads in the presence of 25 μL of 4.7 M tetramethyl ammonium acetate. Sample E was the recovered supernatant of 1 kb DNA molecular weight ladder contacted with silica-coated magnetic beads in the presence of 25 μL of 4.7 M tetramethyl ammonium acetate that was then washed and subjected to a second step of selection with 20 of 4.7 M tetramethyl ammonium acetate.

FIG. 9B compares electrophoretic separation of 1 kb DNA molecular weight ladder samples contacted with silica-coated magnetic beads (SwiftMag® beads) in the presence or absence of 4.7 M tetramethyl ammonium acetate subject to one or more steps of selection. Tetramethyl ammonium acetate at 4.7 M was used as DNA bind modifier in samples B, C, D, and E. Samples B and C were 1 kb DNA molecular weight ladder contacted with silica-coated magnetic beads in the presence 20 µL and 25 µL, respectively, of 4.7 M tetramethyl ammonium acetate. Sample D was the recovered supernatant of 1 kb DNA molecular weight ladder contacted with silica-coated magnetic beads in the presence of 25 µL of 4.7 M tetramethyl ammonium acetate. Sample E was the recovered supernatant of 1 kb DNA molecular weight ladder contacted with silica-coated magnetic beads in the presence of 25 µL of 4.7 M tetramethyl ammonium acetate that was then washed and subjected to a second step of selection with 20 µL of 4.7 M tetramethyl ammonium acetate.

Example 12: Effect of Different Concentrations of Ammonium Anions on Size Selection of DNA on Borosilicate Glass Spin Filters with and without Normalization Fifty microliters of a nucleic acid-containing sample (diluted 1 kb DNA molecular weight ladder) was mixed with 170 µL of ammonium acetate as DNA binding solution and 0-35 µL of each DNA bind modifier. A control sample was made by mixing the same amount of DNA ladder and DNA binding solution without DNA bind modifier. Each of the normalized samples had 45-80 µL of water added to achieve a water and ammonium acetate total volume of 80 µL. The full volume of the reagents was loaded onto a borosilicate glass spin filter and incubated for 2 minutes prior to centrifugation. The spin filter was centrifuged for 1 minute at 10,000×g. The filter was then washed with 300 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 10A:
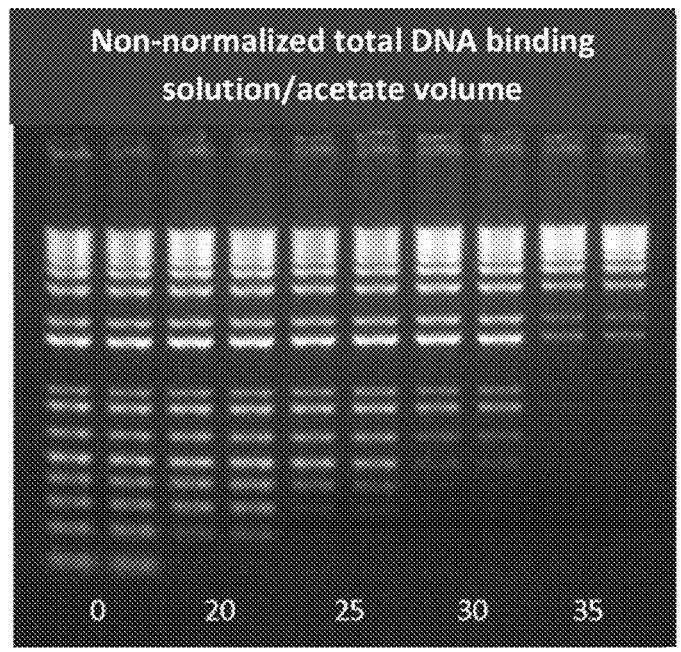
FIG. 10A compares the electrophoretic separation of 1 kb DNA molecular weight ladder samples subjected to increasing amounts of DNA bind modifier (ammonium acetate) during the binding reaction using borosilicate glass spin filters. The amount of ammonium acetate was not normalized against a standard volume of the nucleic binding buffer. In this gel, the nucleic acid binding solution was held constant at 170 μL while DNA bind modifier volumes were varied from 0 to 35 μL.

FIG. 10A compares the electrophoretic separation of 1 kb DNA molecular weight ladder samples subjected to increasing amounts of DNA bind modifier (ammonium acetate) during the binding reaction using borosilicate glass spin filters. The amount of ammonium acetate was not normalized against a standard volume of the nucleic binding buffer. In this gel, the nucleic acid binding solution was held constant at 170 µL while DNA bind modifier volumes were varied from 0 to 35 µL.

Figure 10B:
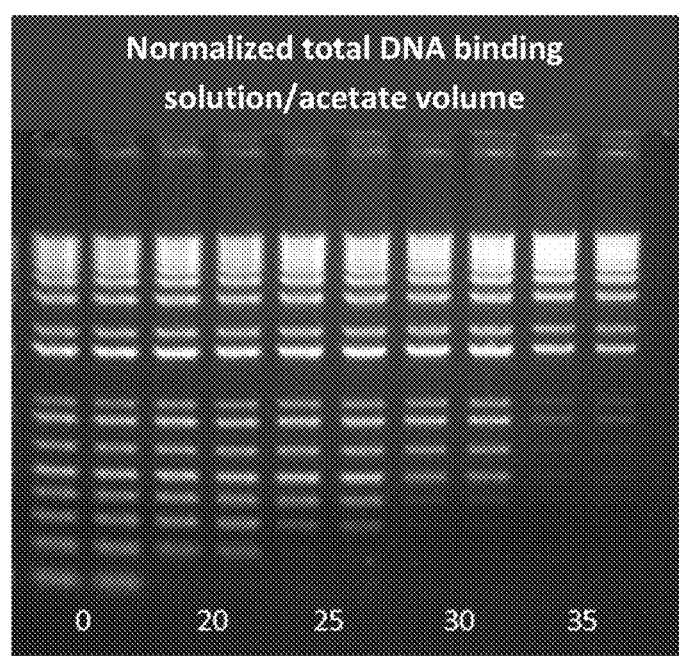
FIG. 10B compares the electrophoretic separation of 1 kb DNA molecular weight ladder samples subjected to increasing amounts of DNA bind modifier (ammonium acetate) during the binding reaction using borosilicate glass spin filters. The amount of nucleic acid binding buffer and ammonium acetate was normalized against a standard volume using water. In this gel, the nucleic acid binding solution was held constant at 170 μL while DNA bind modifier volumes were varied from 0 to 35 μL.

FIG. 10B compares the electrophoretic separation of 1 kb DNA molecular weight ladder samples subjected to increasing amounts of DNA bind modifier (ammonium acetate) during the binding reaction using borosilicate glass spin filters. The amount of nucleic acid binding buffer and ammonium acetate was normalized against a standard volume using water. In this gel, the nucleic acid binding solution was held constant at 170 µL while DNA bind modifier volumes were varied from 0 to 35 µL.

Example 13: Effect of Substituted Carboxylates on Size Selection of DNA on Borosilicate Glass Spin Filters Fifty microliters of a nucleic acid-containing sample (diluted 1 kb DNA molecular weight ladder) was mixed with 170 µL of DNA binding solution and 0-35 µL of each DNA bind modifier. A control sample was made by mixing the same amount of DNA ladder and DNA binding solution without DNA bind modifier. Ammonium acetate, sodium formate, sodium propionate, sodium trifluoroacetate, and sodium trichloroacetate were used as DNA bind modifiers. The full volume of the reagents was loaded onto a borosilicate glass spin filter and incubated for 2 minutes prior to centrifugation. The spin filter was centrifuged for 1 minute at 10,000×g. The filter was then washed with 300 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 11A:
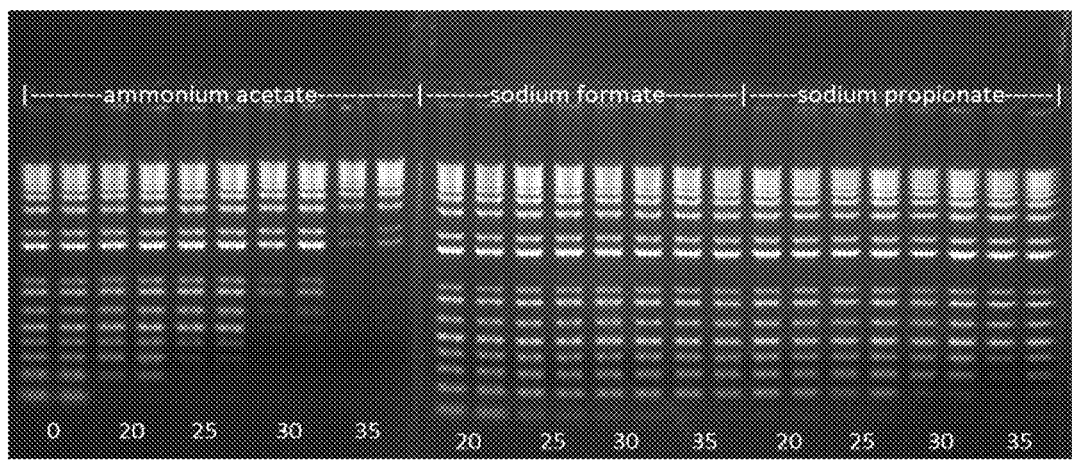
FIG. 11A compares the electrophoretic separation of 1 kb DNA molecular weight ladder samples subjected to increasing amounts of different DNA bind modifiers during the binding reaction using borosilicate glass spin filters. Ammonium acetate, sodium formate, and sodium propionate were used as DNA bind modifiers. In this gel, the nucleic acid binding solution was held constant at 170 µL while DNA bind modifier volumes were varied from 0 to 35 µL.

FIG. 11A compares the electrophoretic separation of 1 kb DNA molecular weight ladder samples subjected to increasing amounts of different DNA bind modifiers during the binding reaction using borosilicate glass spin filters. Ammonium acetate, sodium formate, and sodium propionate were used as DNA bind modifiers. In this gel, the nucleic acid binding solution was held constant at 170 µL while DNA bind modifier volumes were varied from 0 to 35 µL.

Figure 11B:
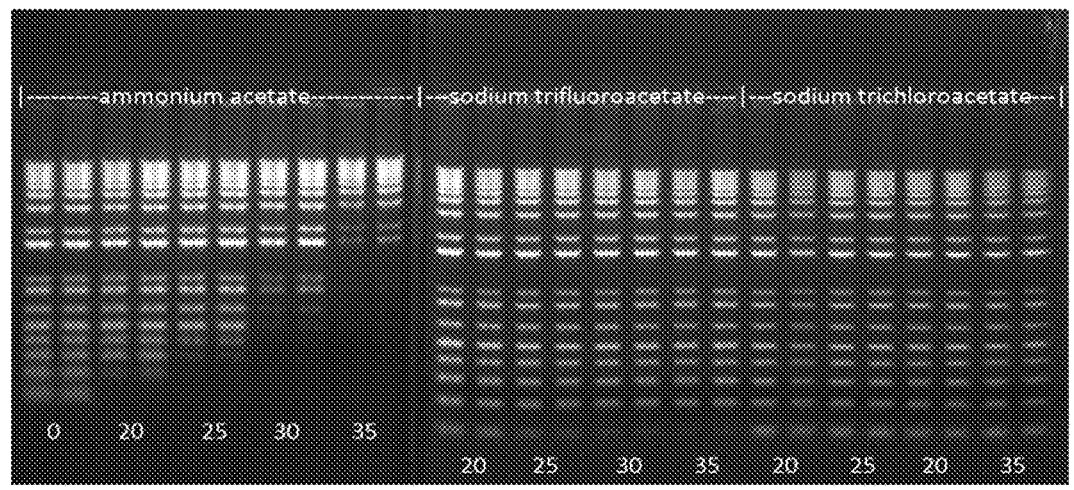
FIG. 11B compares the electrophoretic separation of 1 kb DNA molecular weight ladder samples subjected to increasing amounts of different DNA bind modifiers during the binding reaction using borosilicate glass spin filters. Ammonium acetate, sodium trifluoroacetate, and sodium trichloroacetate were used as DNA bind modifiers. In this gel, the nucleic acid binding solution was held constant at 170 µL while DNA bind modifier volumes were varied from 0 to 35 µL.

FIG. 11B compares the electrophoretic separation of 1 kb DNA molecular weight ladder samples subjected to increasing amounts of different DNA bind modifiers during the binding reaction using borosilicate glass spin filters. Ammonium acetate, sodium trifluoroacetate, and sodium trichloroacetate were used as DNA bind modifiers. In this gel, the nucleic acid binding solution was held constant at 170 µL while DNA bind modifier volumes were varied from 0 to 35 µL.

Example 14: Effect of Different DNA Binding Solutions on Size Selection of DNA on Borosilicate Glass Spin Filters Fifty microliters of a nucleic acid-containing sample (diluted 1 kb DNA molecular weight ladder) was mixed with 170 µL of different DNA binding solution and either 0 or 35 of DNA bind modifier. 4.67 M tetramethyl ammonium acetate was used as DNA bind modifier. Bind A (Guanidine HCl (5.2 M) [50%]+Tris HCl (0.03 M)+99% Isopropanol (8%)), Bind B (Guanidine Thiocyanate (4 M) [47%]+Tris Base (0.1M)+33% Ethanol), Bind C (Guanidine Thiocyanate (6 M, 71%)), and Bind D (2.3 Guan+0.0128 Tris HCl+3.88% isoprop)+56% EtOH) were used as DNA binding solutions. The full volume of the reagents was loaded onto a borosilicate glass spin filter and incubated for 2 minutes prior to centrifugation. The spin filter was centrifuged for 1 minute at 10,000×g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 12:
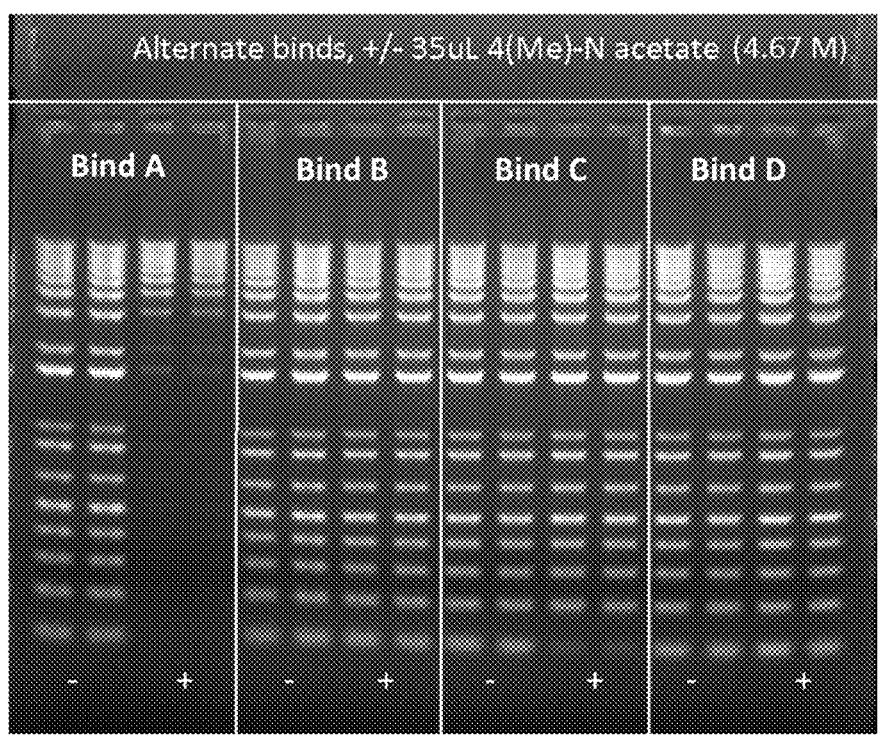
FIG. 12 compares the electrophoretic separation of 1 kb DNA molecular weight ladder samples subjected to different DNA binding buffers in the presence or absence of DNA bind modifier (4.67 M tetramethyl ammonium acetate) during the binding reaction using borosilicate glass spin filters. In this gel, the nucleic acid binding solution was held constant at 170 µL while DNA bind modifier volumes were varied from 0 to 35 µL.

FIG. 12 compares the electrophoretic separation of 1 kb DNA molecular weight ladder samples subjected to different DNA binding solutions in the presence or absence of DNA bind modifier (4.67 M tetramethyl ammonium acetate) during the binding reaction using borosilicate glass spin filters. In this gel, the nucleic acid binding solution was held constant at 170 DNA bind modifier volumes was either 0 or 35 µL.

Example 15: Effect of Different Guanidine Based DNA Binding Solutions on Size Selection of DNA on Borosilicate Glass Spin Filters Fifty microliters of a nucleic acid-containing sample (diluted 1 kb DNA molecular weight ladder) was mixed with 170 µL of different DNA binding solutions and either 0 or 35 of DNA bind modifier. 4.67 M tetramethyl ammonium acetate was used as DNA bind modifier. Guanidine carbonate, guanidine phosphate, guanidine sulfate, and guanidine thiocyanate based solutions were used as DNA binding solutions. The full volume of the reagents was loaded onto a borosilicate glass spin filter and incubated for 2 minutes prior to centrifugation. The spin filter was centrifuged for 1 minute at 10,000×g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 13:
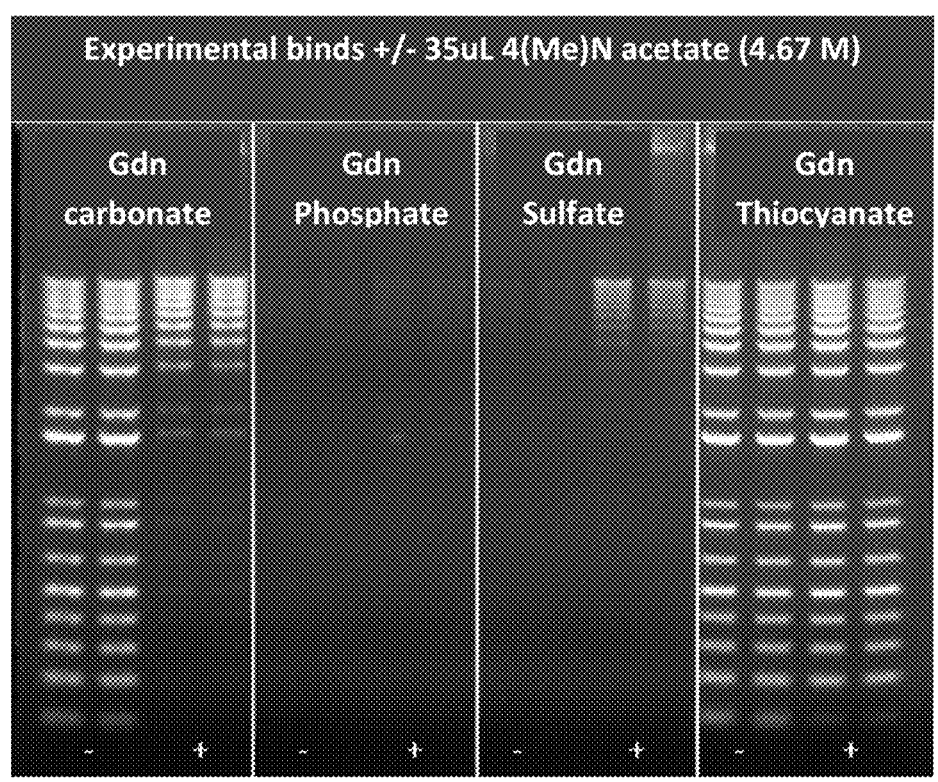
FIG. 13 compares the electrophoretic separation of 1 kb DNA molecular weight ladder samples subjected to different DNA binding solutions in the presence or absence of DNA bind modifier (4.67 M tetramethyl ammonium acetate) during the binding reaction using borosilicate glass spin filters. Guanidine carbonate, guanidine phosphate, guanidine sulfate, and guanidine thiocyanate based solutions were used as DNA binding solutions. In this gel, the nucleic acid binding solution was held constant at 170 DNA bind modifier volumes was either 0 or 35 µL.

FIG. 13 compares the electrophoretic separation of 1 kb DNA molecular weight ladder samples subjected to different DNA binding solutions in the presence or absence of DNA bind modifier (4.67 M tetramethyl ammonium acetate) during the binding reaction using borosilicate glass spin filters. Guanidine carbonate, guanidine phosphate, guanidine sulfate, and guanidine thiocyanate based solutions were used as DNA binding solutions. In this gel, the nucleic acid binding solution was held constant at 170 µL, DNA bind modifier volumes was either 0 or 35 µL.

Example 16: Effect of Ammonium Acetate on Size Selection of gDNA on Borosilicate Glass Spin Filters Fifty microliters of a nucleic acid-containing sample (diluted 1 kb DNA molecular weight ladder or diluted E. coli gDNA) was mixed with 170 µL of different DNA binding solution and 0 to 35 µL of DNA bind modifier. 4.67 M tetramethyl ammonium acetate was used as DNA bind modifier. The full volume of the reagents was loaded onto a borosilicate glass spin filter and incubated for 2 minutes prior to centrifugation. The spin filter was centrifuged for 1 minute at 10,000×g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 14:
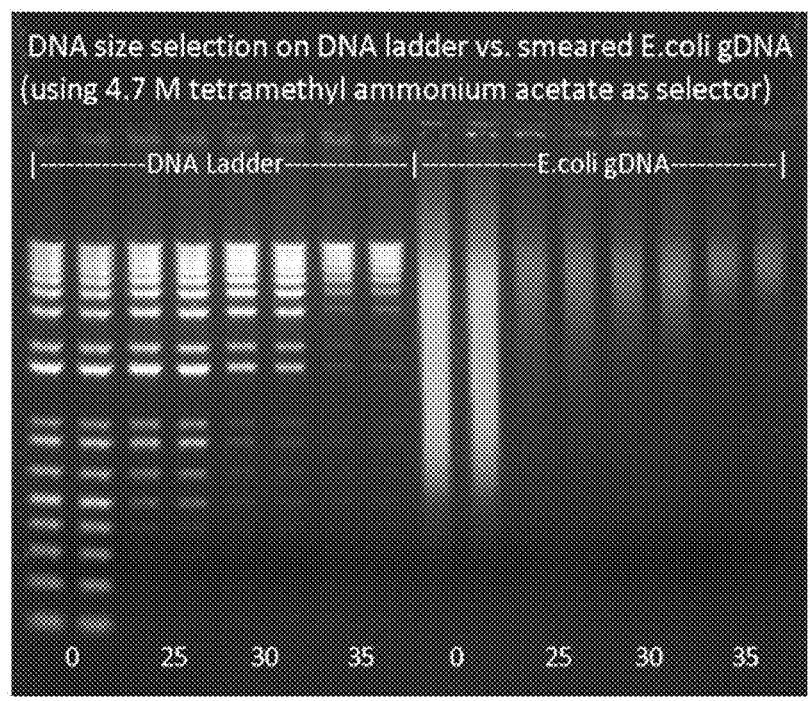
FIG. 14 compares the electrophoretic separation of 1 kb DNA molecular weight ladder and *E. coli* gDNA samples subjected to increasing amounts of 4.67 M tetramethyl ammonium acetate as DNA bind modifier during the binding reaction using borosilicate glass spin filters. In this gel, the nucleic acid binding solution was held constant at 170 µL while DNA bind modifier volumes were varied from 0 to 35 µL.

FIG. 14 compares the electrophoretic separation of 1 kb DNA molecular weight ladder and E. coli gDNA samples subjected to increasing amounts of 4.67 M tetramethyl ammonium acetate as DNA bind modifier during the binding reaction using borosilicate glass spin filters. In this gel, the nucleic acid binding solution was held constant at 170 µL while DNA bind modifier volumes were varied from 0 to 35 µL.

Example 17: Effect of Ammonium Acetate on Size Selection of Primer Dimers on Borosilicate Glass Spin Filters Fifty microliters of a nucleic acid-containing sample (diluted 1 kb DNA molecular weight ladder or diluted PCR reaction) was mixed with 170 µL of DNA binding solution and 0-25 µL of DNA bind modifier. 4.7 M tetramethyl ammonium acetate was used as DNA bind modifier. The full volume of the reagents was loaded onto a borosilicate glass spin filter and incubated for 2 minutes prior to centrifugation. The spin filter was centrifuged for 1 minute at 10,000× g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 15A:
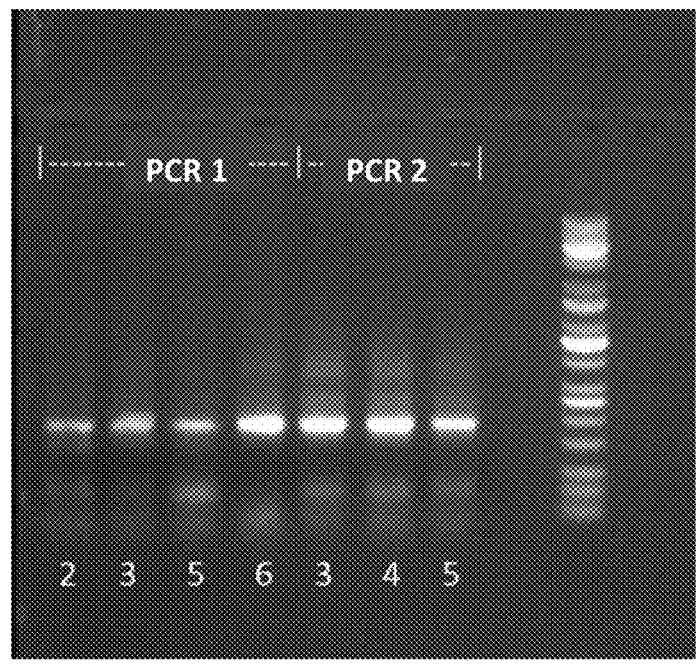
FIG. 15A shows the electrophoretic separation of PCR reactions generated using appropriate primers.

FIG. 15A shows the electrophoretic separation of PCR reactions generated using appropriate primers.

Figure 15B:
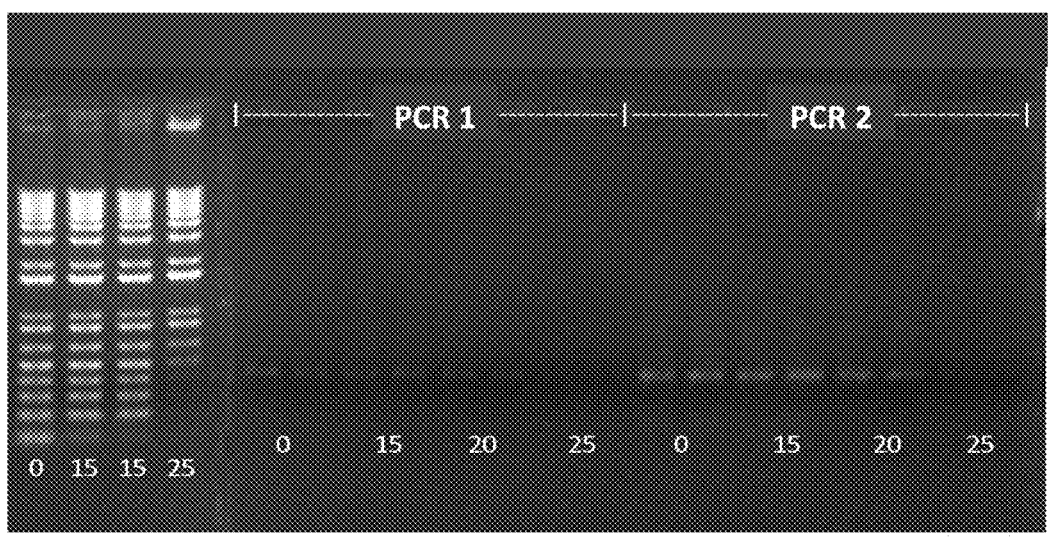
FIG. 15B compares the electrophoretic separation of 1 kb DNA molecular weight ladder and PCR product samples subjected to increasing amounts of 4.7 M tetramethyl ammonium acetate as DNA bind modifier during the binding reaction using borosilicate glass spin filters. In this gel, the nucleic acid binding solution was held constant at 170 µL while DNA bind modifier volumes were varied from 0 to 25 µL.

FIG. 15B compares the electrophoretic separation of 1 kb DNA molecular weight ladder and PCR product samples subjected to increasing amounts of 4.7 M tetramethyl ammonium acetate as DNA bind modifier during the binding reaction using borosilicate glass spin filters. In this gel, the nucleic acid binding solution was held constant at 170 µL while DNA bind modifier volumes were varied from 0 to 25 µL.

Example 18: Effect of Ethanol as Secondary Bind for Recovered Flow Through of Ammonium Acetate Size Selected DNA on Borosilicate Glass Spin Filters Samples of 50 µL of a nucleic acid-containing sample (diluted 1 kb DNA molecular weight ladder was mixed with 170 µL of DNA binding solution and 35 µL of DNA bind modifier. 4.7 M tetramethyl ammonium acetate was used as DNA bind modifier. A control with no selection was prepared with 50 µL of a nucleic acid-containing sample mixed with 170 µL of DNA binding solution. The full volume of the reagents was loaded onto a borosilicate glass spin filter and incubated for 2 minutes prior to centrifugation. The spin filter was centrifuged for 1 minute at 10,000×g. The control with no selection and spin filter from initial bind was set aside. The flow through of samples with DNA bind modifier was recovered and combined with 1 volume, 2 volumes, or 3 volumes of neat EtOH by vortexting. The EtOH and recovered flow through mixtures were loaded onto separate secondary spin columns and centrifuged for 1 minute at 10,000×g. The filters were then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 16:
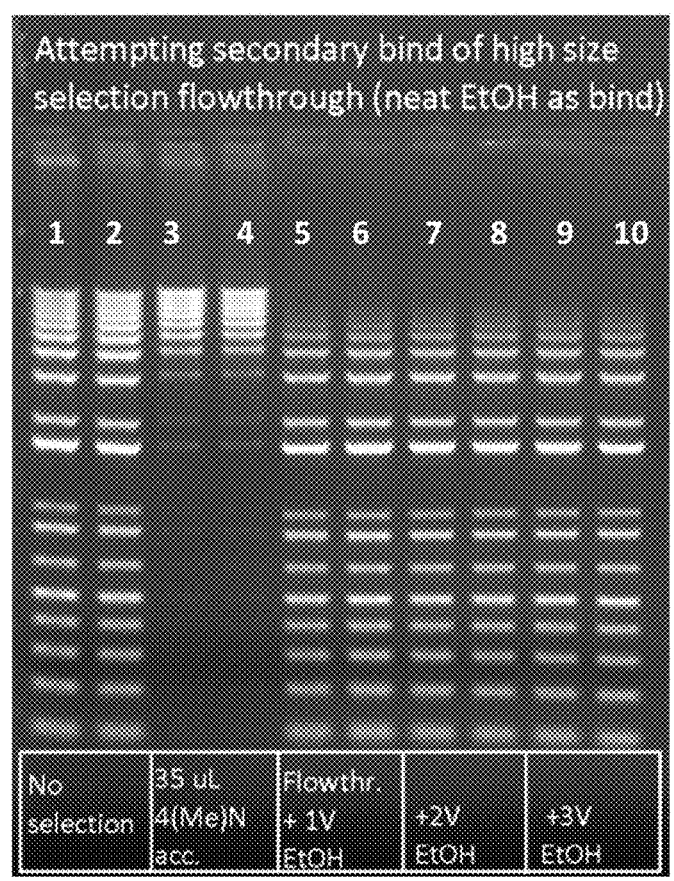
FIG. 16 compares the electrophoretic separation of 1 kb DNA molecular weight ladder samples in the presence or absence of DNA bind modifiers during the initial binding reaction using borosilicate glass spin filters further subjected to a secondary bind. Different volumes of ethanol were used as secondary bind. Samples in lanes 1 and 2 contained the 1 kb DNA molecular weight ladder sample in the absence of any DNA bind modifiers. Samples in lanes 3-10 contained 35 µL of 4.7 M tetramethyl ammonium acetate used as DNA bind modifier in the initial bind. Samples in lanes 5-10 were the recovered flow through of 1 kb DNA molecular weight ladder passed through a borosilicate glass spin filter in the presence of 35 of 4.7 M tetramethyl ammonium acetate subjected to a secondary bind using different volumes of neat ethanol.

FIG. 16 compares the electrophoretic separation of 1 kb DNA molecular weight ladder samples in the presence or absence of DNA bind modifiers during the initial binding reaction using borosilicate glass spin filters further subjected to a secondary bind. Different volumes of ethanol were used as secondary bind. Samples in lanes 1 and 2 contained the 1 kb DNA molecular weight ladder sample in the absence of any DNA bind modifiers. Samples in lanes 3-10 contained 35 µL of 4.7 M tetramethyl ammonium acetate used as DNA bind modifier in the initial bind. Samples in lanes 5-10 were the recovered flow through of 1 kb DNA molecular weight ladder passed through a borosilicate glass spin filter in the presence of 35 µL of 4.7 M tetramethyl ammonium acetate subjected to a secondary bind using different volumes of neat ethanol.

Example 19: Effect of Simultaneous Vs. Stepwise Selection of DNA on Borosilicate Glass Spin Filters The simultaneous selection strategy was performed by first combining nucleic acid-containing sample, DNA binding buffer, and DNA bind modifier in solution and then passing this solution through a spin filter to bind a range of molecular weights. 50 µL of a nucleic acid-containing sample (diluted 1 kb DNA molecular weight ladder) was mixed with 170 µL of DNA binding solution and 0-35 µL of 4.7 tetramethyl ammonium acetate as DNA bind modifier. The full volume of the reagents was loaded onto a borosilicate glass spin filter and incubated for 2 minutes prior to centrifugation. The spin filter was centrifuged for 1 minute at 10,000×g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

The stepwise binding strategy was performed by first binding the nucleic acid-containing sample to a spin filter (using DNA binding solution without DNA bind modifier) and second, washing the spin filter with a mixture of DNA binding solution and DNA bind modifier (on-filter selection). First, 50 µL of a nucleic acid-containing sample (diluted 1 kb DNA molecular weight ladder) mixed with 170 µL of DNA binding buffer was loaded onto a borosilicate glass spin filter. The spin filter was centrifuged for 1 minute at 10,000×g and the flow through was discarded. Second, a mixture of 170 µL of DNA binding buffer and 0-35 µL of 4.7 tetramethyl ammonium acetate as DNA bind modifier was loaded onto the spin filter. The filter and mixture was incubated for 2 minutes prior to centrifugation then centrifuged for 1 minute at 10,000×g. The filter was washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 17:
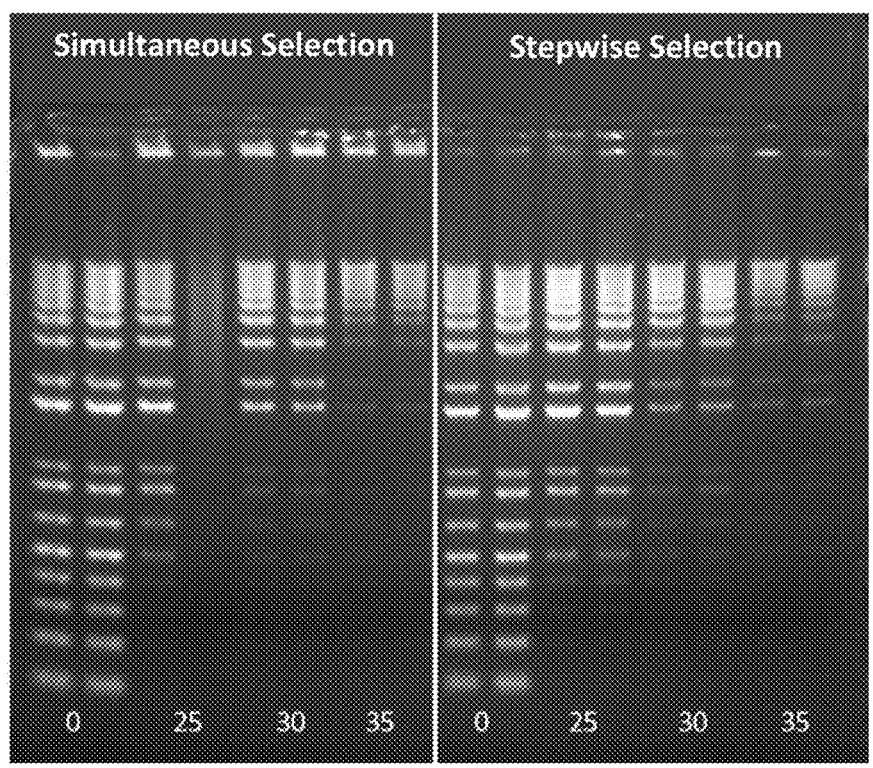
FIG. 17 compares the electrophoretic separation of 1 kb DNA molecular weight ladder samples in the presence of increasing amounts of 4.67 M tetramethyl ammonium acetate as DNA bind modifiers using borosilicate glass spin filters with a simultaneous selection strategy and a stepwise selection strategy. DNA bind modifier was added to the DNA sample prior to loading on the spin filter for simultaneous selection and added to the spin filter bound with DNA for stepwise selection (on-filter selection). In this gel, DNA bind modifier volumes were varied from 0 to 35 µL.

FIG. 17 compares the electrophoretic separation of 1 kb DNA molecular weight ladder samples in the presence of increasing amounts of 4.67 M tetramethyl ammonium acetate as DNA bind modifiers using borosilicate glass spin filters with a simultaneous selection strategy and a stepwise selection strategy. DNA bind modifier was added to the DNA sample prior to loading on the spin filter for simultaneous selection and added to the spin filter bound with DNA for stepwise selection (on-filter selection). In this gel, DNA bind modifier volumes were varied from 0 to 35 µL.

Example 20: Effect of Stepwise Selection of DNA on Borosilicate Glass Spin Filters for Eliminating Low Molecular Weight DNA For the initial binding reaction, 50 µL of a nucleic acid-containing sample (diluted 1 kb DNA molecular weight ladder) was mixed with 170 µL of DNA binding buffer and 0, 25 or 35 µL of 4.7 tetramethyl ammonium acetate as DNA bind modifier. The filter and mixture was incubated for 2 minutes prior to centrifugation then centrifuged for 1 minute at 10,000×g. The flow through was combined with an equal volume of neat ethanol and set aside (Sample C). For the secondary binding reaction, 170 µL of DNA binding buffer and 25 or 35 µL of 4.7 tetramethyl ammonium acetate as DNA bind modifier was loaded into the column (Sample B). The filter and mixture was incubated for 2 minutes prior to centrifugation then centrifuged for 1 minute at 10,000×g. The flow through was combined with an equal volume of neat ethanol and set aside (Sample D). Samples C and D were added to a new spin column and incubated for 2 minutes, then centrifuged for 1 minute at 10,000×g. All samples were washed with 500 µL of wash buffer via 1 minute of centrifugation at 10,000×g. The spin filter was centrifuged again for 2 minutes at 16,000×g to spin dry. The bound DNA fragments were incubated with 50 of elution buffer for 2 minutes and centrifuged at 10,000×g for 1 minute to elute. The eluents were analyzed by agarose gel electrophoresis.

Figure 18:
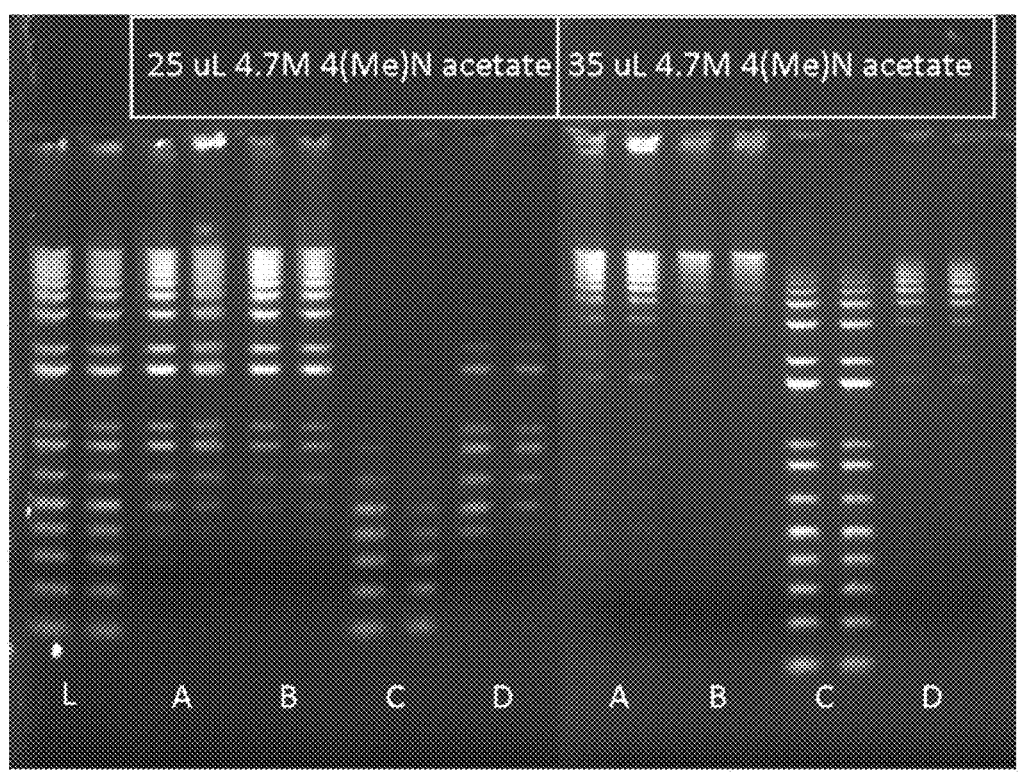
FIG. 18 compares the electrophoretic separation of 1 kb DNA molecular weight ladder samples in the presence of different amounts of 4.67 M tetramethyl ammonium acetate as DNA bind modifier using borosilicate glass spin filters in a stepwise binding method. Sample A was 1 kb DNA molecular weight ladder subjected to 4.7 M tetramethyl ammonium acetate during an initial binding reaction using borosilicate glass spin filters. Sample B was 1 kb DNA molecular weight ladder subjected to 4.7 M tetramethyl ammonium acetate during an initial binding reaction using borosilicate glass spin filters subjected to a secondary binding reaction using the same DNA bind modifier. Sample C was the recovered flow through of Sample A. Sample D was the recovered flow through of Sample B. In this gel, the nucleic acid binding solution was held constant at 170 µL while DNA bind modifier volumes were varied from 25 to 35 µL.

FIG. 18 compares the electrophoretic separation of 1 kb DNA molecular weight ladder samples in the presence of different amounts of 4.67 M tetramethyl ammonium acetate as DNA bind modifier using borosilicate glass spin filters in a stepwise binding method. Sample A was 1 kb DNA molecular weight ladder subjected to 4.7 tetramethyl ammonium acetate during an initial binding reaction using borosilicate glass spin filters. Sample B was 1 kb DNA molecular weight ladder subjected to 4.7 tetramethyl ammonium acetate during an initial binding reaction using borosilicate glass spin filters subjected to a secondary binding reaction using the same DNA bind modifier. Sample C was the recovered flow through of Sample A. Sample D was the recovered flow through of Sample B. In this gel, the nucleic acid binding solution was held constant at 170 µL while DNA bind modifier volumes were varied from 25 to 35 µL.

Example 21: Effect of Different Concentrations of Ethanol as Secondary Bind for Recovered Flow Through of Ammonium Acetate Size Selected DNA on Borosilicate Glass Spin Filters Samples of 50 µL of a nucleic acid-containing sample (diluted 1 kb DNA molecular weight ladder was mixed with 170 µL of DNA binding buffer and 35 µL of DNA bind modifier. 4.7 M tetramethyl ammonium acetate was used as DNA bind modifier. A control with no selection was prepared with 50 µL of a nucleic acid-containing sample mixed with 170 µL of DNA binding buffer. The full volume of the reagents was loaded onto a borosilicate glass spin filter and incubated for 2 minutes prior to centrifugation. The spin filter was centrifuged for 1 minute at 10,000×g. The control with no selection and spin filter from initial bind was set aside. The flow through of samples with DNA bind modifier was recovered and combined with 50%, 70%, 90%, or 100% EtOH. The EtOH and recovered flow through mixtures were loaded onto separate secondary spin columns and centrifuged for 1 minute at 10,000×g. The filters were then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 19:
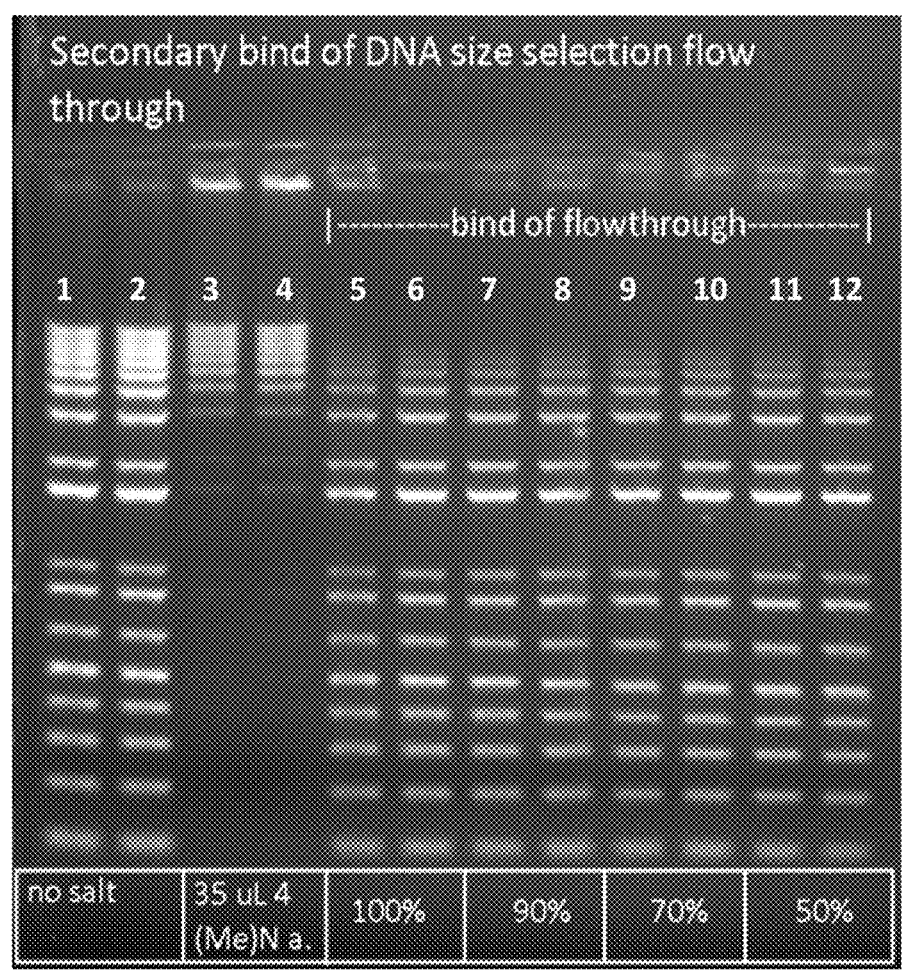
FIG. 19 compares the electrophoretic separation of 1 kb DNA molecular weight ladder samples in the presence or absence of DNA bind modifiers during the initial binding reaction using borosilicate glass spin filters and further subjected to a secondary bind. Different concentrations of ethanol were used as secondary bind. Samples in lanes 1 and 2 contained the 1 kb DNA molecular weight ladder sample in the absence of any DNA bind modifiers. Samples in lanes 3-12 contained 35 µL 4.7 M tetramethyl ammonium acetate used as DNA bind modifier in the initial bind. Samples in lanes 5-12 were the recovered flow through of 1 kb DNA molecular weight ladder passed through a borosilicate glass spin filter in the presence of 35 µL of 4.7 M tetramethyl ammonium acetate subjected to a second bind using different concentrations of ethanol.

FIG. 19 compares the electrophoretic separation of 1 kb DNA molecular weight ladder samples in the presence or absence of DNA bind modifiers during the initial binding reaction using borosilicate glass spin filters and further subjected to a secondary bind. Different concentrations of ethanol were used as secondary bind. Samples in lanes 1 and 2 contained the 1 kb DNA molecular weight ladder sample in the absence of any DNA bind modifiers. Samples in lanes 3-12 contained 35 µL 4.7 M tetramethyl ammonium acetate used as DNA bind modifier in the initial bind. Samples in lanes 5-12 were the recovered flow through of 1 kb DNA molecular weight ladder passed through a borosilicate glass spin filter in the presence of 35 µL of 4.7 M tetramethyl ammonium acetate subjected to a second bind using different concentrations of ethanol.

Example 22: Effect of Diluting Recovered Flow Through of Ammonium Acetate Size Selected DNA on Borosilicate Glass Spin Filters During Secondary Bind Samples of 50 µL of a nucleic acid-containing sample (diluted 1 kb DNA molecular weight ladder was mixed with 170 µL of DNA binding buffer and 35 µL of DNA bind modifier. 4.7 M tetramethyl ammonium acetate was used as DNA bind modifier. A control with no selection was prepared with 50 µL of a nucleic acid-containing sample mixed with 170 µL of DNA binding buffer. The full volume of the reagents was loaded onto a borosilicate glass spin filter and incubated for 2 minutes prior to centrifugation. The spin filter was centrifuged for 1 minute at 10,000×g. The control with no selection and spin filter from initial bind was set aside. The flow through of samples with DNA bind modifier was recovered and combined with nothing, 1 volume of neat ethanol, 1 volume of water, 2 volumes of water, or 3 volumes of water. The recovered flow through mixtures were loaded onto separate secondary spin columns and centrifuged for 1 minute at 10,000×g. The filters were then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 20A:
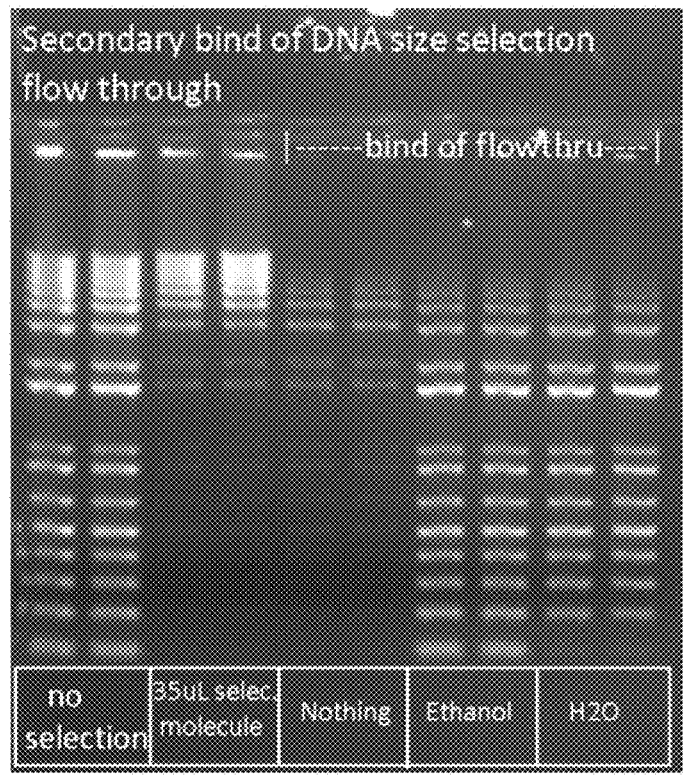
FIG. 20A compares the electrophoretic separation of 1 kb DNA molecular weight ladder samples in the presence or absence of DNA bind modifier (4.67 M tetramethyl ammonium acetate) during the initial binding reaction using borosilicate glass spin filters and further subjected to a secondary bind. During the secondary bind, the flow through was not mixed with other solutions, mixed with ethanol, or with mixed with water.

FIG. 20A compares the electrophoretic separation of 1 kb DNA molecular weight ladder samples in the presence or absence of DNA bind modifier (4.67 M tetramethyl ammonium acetate) during the initial binding reaction using borosilicate glass spin filters and further subjected to a secondary bind. During the secondary bind, the flow through was not mixed with other solutions, mixed with ethanol, or with mixed with water.

Figure 20B:
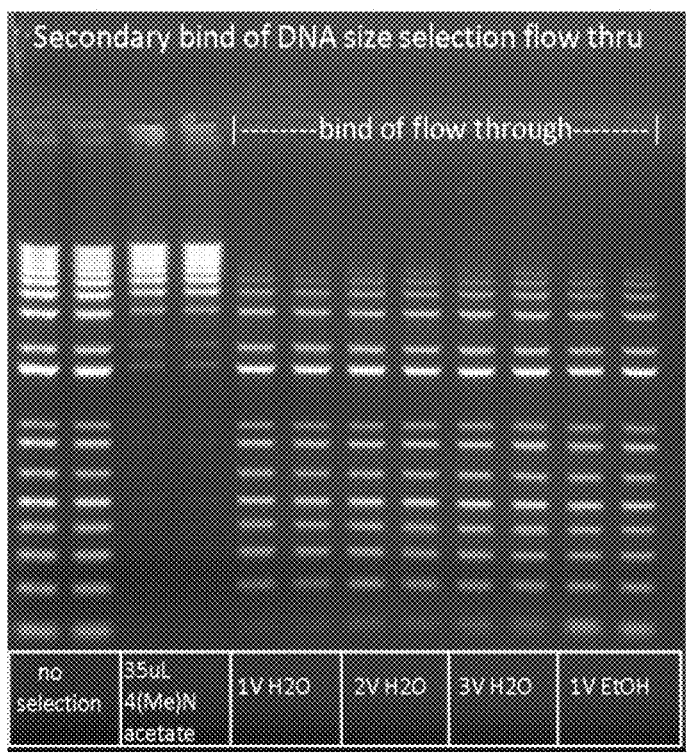
FIG. 20B compares the electrophoretic separation of 1 kb DNA molecular weight ladder samples in the presence or absence of DNA bind modifier (4.67 M tetramethyl ammonium acetate) during the initial binding reaction using borosilicate glass spin filters and further subjected to a secondary bind. During the secondary bind, the flow through was diluted with 1 volume of water, 2 volumes of water, 3 volumes of water or 1 volume of EtOH.

FIG. 20B compares the electrophoretic separation of 1 kb DNA molecular weight ladder samples in the presence or absence of DNA bind modifier (4.67 M tetramethyl ammonium acetate) during the initial binding reaction using borosilicate glass spin filters and further subjected to a secondary bind. During the secondary bind, the flow through was diluted with 1 volume of water, 2 volumes of water, 3 volumes of water or 1 volume of EtOH.

Example 23: Effect of DNA Binding Buffers with Different Guanidine HCl Concentrations on DNA Binding on Borosilicate Glass Spin Filters Fifty microliters of a nucleic acid-containing sample (diluted 1 kb DNA molecular weight ladder) was mixed with 170 µL of different DNA binding buffers. DNA binding buffers with 0.375 M, 0.75 M, 1.5 M, 2 M, and 3 M guanidine HCl concentrations were used. The full volume of the reagents was loaded onto a borosilicate glass spin filter and incubated for 2 minutes prior to centrifugation. The spin filter was centrifuged for 1 minute at 10,000×g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

Figure 21A:
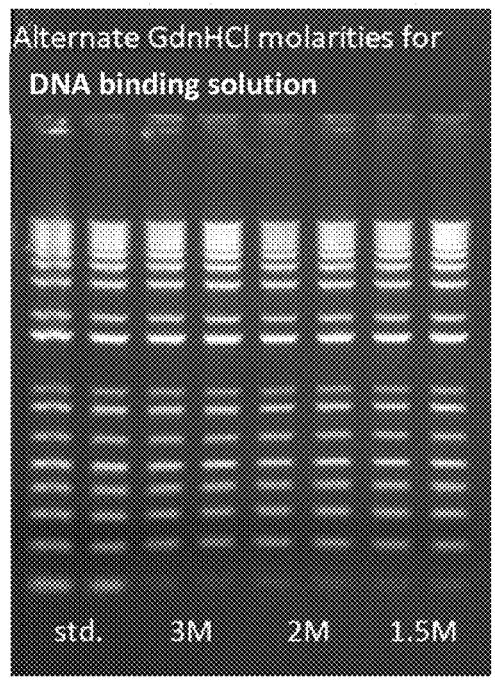
FIG. 21A compares the electrophoretic separation of 1 kb DNA molecular weight ladder samples subjected to DNA binding solutions with different guanidine HCl concentrations during the binding reaction using borosilicate glass spin filters. Nucleic acid binding buffers with 1.5 M, 2 M, and 3 M guanidine HCl were used. In this gel, the different nucleic acid binding solutions was held constant at 170 µL and DNA sample was held constant at 50 µL.

FIG. 21A compares the electrophoretic separation of 1 kb DNA molecular weight ladder samples subjected to DNA binding buffers with different guanidine HCl concentrations during the binding reaction using borosilicate glass spin filters. Nucleic acid binding buffers with 1.5 M, 2 M, and 3 M Guanidine HCl were used. In this gel, the different nucleic acid binding solutions was held constant at 170 µL and DNA sample was held constant at 50 µL.

Figure 21B:
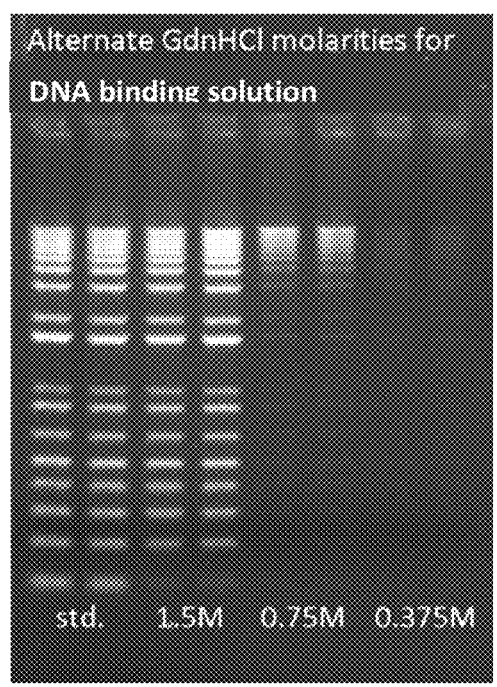
FIG. 21B compares the electrophoretic separation of 1 kb DNA molecular weight ladder samples subjected to DNA binding solutions with different guanidine HCl concentrations during the binding reaction using borosilicate glass spin filters. Nucleic acid binding buffers with 0.375 M, 0.75

FIG. 21B compares the electrophoretic separation of 1 kb DNA molecular weight ladder samples subjected to DNA binding buffers with different guanidine HCl concentrations during the binding reaction using borosilicate glass spin filters. Nucleic acid binding buffers with 0.375 M, 0.75 M, and 1.5 M guanidine HCl were used. In this gel, the different nucleic acid binding solutions was held constant at 170 µL and DNA sample was held constant at 50 µL.

Example 24: Effect of Different Tetramethyl Ammonium Acetate Concentrations on Size Selection of DNA on Borosilicate Glass Spin Filters Fifty microliters of a nucleic acid-containing sample (diluted 1 kb DNA molecular weight ladder) was mixed with 170 µL of DNA binding buffer and 0-35 µL of each concentration of DNA bind modifier. A control sample was made by mixing the 50 µL DNA ladder and 170 µL of DNA binding buffer without DNA bind modifier. 4.7 M, 3.8 M, and 3 M tetramethyl ammonium acetate were used as DNA bind modifiers. The full volume of the reagents was loaded onto a borosilicate glass spin filter and incubated for 2 minutes prior to centrifugation. The spin filter was centrifuged for 1 minute at 10,000×g. The filter was then washed with 300 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

FIG. 22A compares the electrophoretic separation of 1 kb DNA molecular weight ladder samples subjected to different concentrations of DNA bind modifier during the binding reaction using borosilicate glass spin filters. Increasing amounts of 4.7 M and 3.8 M tetramethyl ammonium acetate were used as DNA bind modifiers. In this gel, the nucleic acid binding solution was held constant at 170 µL while DNA bind modifier volumes were varied from 0 to 35 µL.

FIG. 22B compares the electrophoretic separation of 1 kb DNA molecular weight ladder samples subjected to increasing amounts of DNA bind modifier during the binding reaction using borosilicate glass spin filters. 3 M tetramethyl ammonium acetate was used as DNA bind modifier. In this gel, the nucleic acid binding solution was held constant at 170 µL while DNA bind modifier volumes were varied from 0 to 35 µL.

Example 25: Effect of DNA Binding Buffers with Different Guanidine HCl Concentrations on Size Selection of DNA on Borosilicate Glass Spin Filters Fifty microliters of a nucleic acid-containing sample (diluted 1 kb DNA molecular weight ladder) was mixed with 170 µL of different DNA binding solutions and 0-35 µL of 4.7 M tetramethyl ammonium acetate. Standard DNA binding solution and DNA binding solutions with 1.5 M and 3 M guanidine HCl concentrations were used. The full volume of the reagents was loaded onto a borosilicate glass spin filter and incubated for 2 minutes prior to centrifugation. The spin filter was centrifuged for 1 minute at 10,000×g. The filter was then washed with 300 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

FIG. 23 compares the electrophoretic separation of 1 kb DNA molecular weight ladder samples subjected to DNA binding solutions with different guanidine HCl concentrations in the presence or absence of increasing amounts of DNA bind modifier (4.67 M tetramethyl ammonium acetate) during the binding reaction using borosilicate glass spin filters. DNA binding solutions with 1.5 M and 3 M Guanidine HCl were used. In this gel, the different DNA binding solutions was held constant at 170 µL and DNA sample was held constant at 50 µL.

Example 26: Effect of Different Concentrations of Diammonium Phosphate (DAP) on Size Selection of DNA on Borosilicate Glass Spin Filters Fifty microliters of a nucleic acid-containing sample (diluted 1 kb DNA molecular weight ladder) was mixed with 170 µL of DNA binding buffer and 0-35 µL of each DNA bind modifier. A control sample was made by mixing the 50 µL DNA ladder and 170 µL of DNA binding buffer without DNA bind modifier. Different dilutions of 4.03 M DAP (1-100%) were used as DNA bind modifiers. The full volume of the reagents was loaded onto a borosilicate glass spin filter and incubated for 2 minutes prior to centrifugation. The spin filter was centrifuged for 1 minute at 10,000×g. The filter was then washed with 500 µL of wash buffer via 1 minute of centrifugation at 10,000×g. The spin filter was centrifuged again for 2 minutes at 16,000×g to spin dry. The bound DNA fragments were incubated with 50 µL of elution buffer for 2 minutes and centrifuged at 10,000×g for 1 minute to elute. The eluents were analyzed by agarose gel electrophoresis.

FIG. 24A compares the electrophoretic separation of 1 kb DNA molecular weight ladder samples in the absence or presence of increasing amounts of diammonium phosphate (DAP) during the binding reaction using borosilicate glass spin filters. Different dilutions of 4.03 M DAP were used as DNA bind modifier. 50 µL of DNA ladder was combined with 170 of DNA binding solution and DAP amount was kept constant at 35 µL (DAP dilutions were varied from 1 to 100%).

FIG. 24B compares the electrophoretic separation of 1 kb DNA molecular weight ladder samples in the absence or presence of increasing amounts of diammonium phosphate (DAP) during the binding reaction using borosilicate glass spin filters. Different dilutions of 4.03 M DAP were used as DNA bind modifier. 50 µL of DNA ladder was combined with 170 of nucleic acid binding solution and DAP amount was kept constant at 35 µL (DAP dilutions were varied from 30 to 50%).

FIG. 24C compares the electrophoretic separation of 1 kb DNA molecular weight ladder samples in the absence or presence of increasing amounts of diammonium phosphate (DAP) during the binding reaction using borosilicate glass spin filters. Different dilutions of 4.03 M DAP were used as DNA bind modifier. 50 µL of DNA ladder was combined with 170 of nucleic acid binding solution and DAP amount was kept constant at 35 µL (DAP dilutions were varied from 25 to 100%).

Example 27: Effect of Increasing Concentrations of Different DNA Bind Modifiers on Size Selection of DNA on Silica-Coated Magnetic Beads Fifty microliters of a nucleic acid-containing sample (e.g., diluted 1 kb DNA molecular weight ladder) was mixed with 0-35 µL of DNA bind modifier and 170 µL DNA binding buffer. 4.7 M tetramethyl ammonium acetate and 2.02 M diammonium phosphate (DAP) were used as DNA bind modifier. To the mixture, 25 µL of SwiftMag® beads was added and the sample was mixed with gentle vortexing every 2 minutes for a total of 10 minutes. The reaction was placed on an appropriate magnet to collect the SwiftMag® beads for 2 minutes and the supernatant was removed. The collected beads were washed with 500 µL of wash buffer by repeatedly pipetting. The tubes were placed on the magnetic rack for 2 minutes and the supernatant was removed. The tubes were incubated at 55 degrees Celsius, then 50 µL of elution buffer was added and the tubes were incubated for 10 minutes (vortexing every 2 minutes). The eluent was transferred to clean tubes and analyzed by agarose gel electrophoresis.

FIG. 25 compares electrophoretic separation of 1 kb DNA molecular weight ladder samples contacted with silica-coated magnetic beads (SwiftMag® beads) in the presence or absence of DNA bind modifier. Different amounts of 4.7 M tetramethyl ammonium acetate and 2.02 M diammonium phosphate (DAP) were used as DNA bind modifier. 50 µL of DNA ladder was combined with 170 µL DNA Binding Solution and 0-35 µL of DNA bind modifier.

Example 28: Effect of Membrane Pretreatment with
DNA Bind Modifier on Size Selection of DNA on
Borosilicate Glass Spin Filters To pretreat columns, the spin filters in Samples D and E were loaded with a mixture of 35 μL of DNA bind modifier and 170 μL DNA binding buffer. 4.7 M tetramethyl ammonium acetate and 2.02 M diammonium phosphate (DAP) were used as DNA bind modifiers. To pretreat columns for Samples F and G, spin filters were loaded with a 170 of DNA bind modifier. The solutions were incubated with the spin filter for 2 minutes then centrifuged for 1 minute at 10,000×g.

Fifty microliters of a nucleic acid-containing sample (diluted 1 kb DNA molecular weight ladder) was mixed with 170 μL of different DNA binding buffers in the presence or absence of 35 μL of DNA bind modifier. This solution was loaded onto to either non-pretreated spin filters for Samples B and C, or to each of the pretreated spin filters for Samples D, E, F, and G. The solutions were incubated for 2 minutes then centrifuged for 1 minute at 10,000×g. The filter was then washed with 500 μL of wash buffer via 1 minute of centrifugation at 10,000×g. The spin filter was centrifuged again for 2 minutes at 16,000×g to spin dry. The bound DNA fragments were incubated with 50 μL of elution buffer for 2 minutes and centrifuged at 10,000×g for 1 minute to elute. The eluents were analyzed by agarose gel electrophoresis.

FIG. 26 compares the electrophoretic separation of 1 kb DNA molecular weight ladder samples in the presence or absence of DNA bind modifier during the binding reaction using borosilicate glass spin filters with or without pretreatment with the DNA bind modifier. 4.7 M tetramethyl ammonium acetate and 2.02 M diammonium phosphate (DAP) were used as DNA bind modifiers. Sample A was a control sample that did not contain DNA bind modifier. 50 μL of DNA ladder was combined with 170 μL of DNA binding solution and 35 μL of DNA bind modifier in Samples B and C. In Samples D and E, a mixture of 50 μL of DNA ladder, 170 μL of DNA binding solution, and 35 μL of the indicated DNA bind modifier was subjected to a spin filter pretreated with 35 μL of the same DNA bind modifier and 170 μL DNA binding solution. In Samples F and G, a mixture of 50 μL of DNA ladder, 170 μL of DNA binding solution, and 35 μL of the indicated DNA bind modifier was subjected to a spin filter pretreated with 170 of the same DNA bind modifier.

The invention claimed is:
1. A method of selectively isolating target nucleic acid molecules from a nucleic acid-containing sample, wherein the target nucleic acid molecules are within a particular molecular size range and non-target nucleic acid molecules are outside the molecular size range, comprising:
 a) contacting a sample comprising nucleic acid molecules with a first matrix in the absence of a small-molecule modulator such that both target and non-target nucleic acid molecules bind to the first matrix;
 b) washing the first matrix in the presence of a first small-molecule modulator,
 wherein the first small-molecule modulator is present in a sufficient concentration that nucleic acid molecules of molecular size above the upper limit of the molecular size range are selectively retained on the first matrix and nucleic acid molecules of molecular size below the upper limit of the molecular size range are released from the first matrix;
 c) collecting all or a portion of the sample that is released from the first matrix;
 d) contacting all or the portion of the sample that is released from the first matrix with a second matrix in the presence of a second small-molecule modulator,
 wherein the second small-molecule modulator is present in a sufficient concentration that nucleic acid molecules of the molecular size range selectively bind to the second matrix and nucleic acid molecules of molecular size below the lower limit of the molecular size range do not bind to the second matrix,
 wherein the first small-modulator and the second small-modulator are independently:
  (i) a compound of formula (Ib) or a hydrate thereof:

wherein
   $R^2$ is a phosphate or a phosphonic acid,
   M is a metal or $N(R^a)_4$,
   each $R^a$ is independently H or alkyl, and
   n is 1, 2, or 3; or
  (ii) a carboxylate compound of formula (I) or a hydrate thereof:

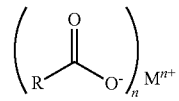

wherein
   R is selected from the group consisting of H, substituted or unsubstituted $C_1$-$C_8$ alkyl, substituted or unsubstituted $C_1$-$C_8$ alkenyl, and substituted or unsubstituted $C_1$-$C_8$ alkynyl,
   M is a metal or $N(R^a)_4$,
   each $R^a$ is independently H or alkyl, and
   n is 1, 2, or 3; and
 wherein the first matrix and the second matrix independently comprise silica, borosilicate glass, silicon dioxide, silicon dioxide-coated magnetic beads, or a metal oxide.
2. The method of claim 1, wherein the first small-molecule modulator is a carboxylate compound of formula (I).
3. The method of claim 1, wherein the second small-molecule modulator is a carboxylate compound of formula (I).
4. The method of claim 1, wherein the concentration of the first small-molecule modulator is greater than the concentration of the second small-molecule modulator.
5. The method of claim 1, further comprising
 washing the second matrix to remove the unbound nucleic acid, and/or
 eluting the bound nucleic acid molecules from the second matrix.
6. The method of claim 1, wherein the first matrix, the second matrix, or both the first and second matrices are borosilicate glass spin filters or comprise a metal oxide selected from iron oxide and magnesium oxide.
7. The method of claim 1, wherein the first matrix and the second matrix are the same in composition.
8. The method of claim 1, wherein the first matrix and the second matrix are different in composition.
9. The method of claim 1, wherein the first small-molecule modulator, the second small-molecule modulator, or both modulators comprise an ammonium or substituted ammonium moiety, acetate, or both an ammonium or substituted ammonium moiety and acetate.

10. The method of claim 1, wherein the first small-molecule modulator, the second small-molecule modulator, or both modulators are of formula (Ib) or a hydrate thereof.

11. The method of claim 10, wherein R2 is phosphonoacetic acid.

12. The method of claim 1, wherein the first small-molecule modulator, the second small-molecule modulator, or both modulators are a carboxylate compound of formula (I) or a hydrate thereof.

13. The method of claim 12, wherein R is unsubstituted $C_1$-$C_8$ alkyl.

14. The method of claim 13, wherein R is $CH_3$.

15. The method of claim 10, wherein $M^{n+}$ is $Na^+$, $K^+$, $Ca^{2+}$, $Mg^{2+}$, $Al^{3+}$, or $NH_4^+$.

16. The method of claim 12, wherein $M'''^+$ is $Na^+$, $Li^+$, $K^+$, $Ca^{2+}$, $Mg^{2+}$, $Al^{3+}$, or $NH_4^+$.

17. The method of claim 1, wherein the first small-molecule modulator, the second small-molecule modulator, or both modulators are ammonium acetate or sodium acetate.

18. The method of claim 1, wherein the first small-molecule modulator, the second small-molecule modulator, or both modulators are selected from diammonium phosphate, ammonium phosphate dibasic, monopotassium phosphate, dipotassium phosphate, tripotassium phosphate, monosodium phosphate, disodium phosphate, trisodium phosphate, 3-aminopropylphosphonic acid, and (aminomethyl)phosphonic acid.

19. The method of claim 1, wherein the first small-molecule modulator, the second small-molecule modulator, or both modulators are in a solution.

20. The method of claim 19, wherein the solution comprises 7.5 M ammonium acetate, 5.2 M guanidine hydrochloride, and 30 mM Tris-HCl.

21. The method of claim 19, wherein the solution further comprises guanidine hydrochloride and Tris-HCl.

22. The method of claim 21, wherein the solution further comprises isopropanol.

23. The method of claim 19, wherein the solution comprises ammonium acetate, guanidine hydrochloride, and Tris-HCl.

24. The method of claim 1, wherein increasing the concentration of the first small-molecule modulator increases the molecular weight cut-off for nucleic acid molecules that elute from the first matrix, and/or increasing the concentration of the second small molecule modulator increases the molecular weight cut-off for nucleic acid molecules that bind to the second matrix.

25. The method of claim 1, wherein the first small-molecule modulator and the second small-molecule modulator are the same in composition.

26. The method of claim 1, wherein the nucleic acid comprises DNA.

27. The method of claim 1, wherein the nucleic acid comprises RNA.

28. The method of claim 1, wherein the first small-molecule modulator, the second small-molecule modulator, or both modulators are a phosphonoacetate.

* * * * *

UNITED STATES PATENT AND TRADEMARK OFFICE
CERTIFICATE OF CORRECTION

PATENT NO. : 11,725,203 B2
APPLICATION NO. : 16/953857
DATED : August 15, 2023
INVENTOR(S) : Vince Moroney et al.

It is certified that error appears in the above-identified patent and that said Letters Patent is hereby corrected as shown below:

In the Claims

Column 44, Claim 1, Lines 13-14:
"$(R^2)_n M^{n+}$" should read: --$(R^2)_n M^{n+}$ (Ib)--.

Column 45, Claim 15, Line 13:
"$M^{n+}$ is $Na^+$, $K^+$," should read: --$M^{n+}$ is $Na^+$, $Li^+$, $K^+$,--.

Signed and Sealed this
Fourth Day of February, 2025

Coke Morgan Stewart
*Acting Director of the United States Patent and Trademark Office*